(12) United States Patent
Ammann et al.

(10) Patent No.: US 8,702,715 B2
(45) Date of Patent: Apr. 22, 2014

(54) METHOD AND APPARATUS FOR PERFORMING AN OPEN WEDGE, HIGH TIBIAL OSTEOTOMY

(75) Inventors: Kelly Ammann, Boulder, CO (US);
Vincent P. Novak, Longmont, CO (US);
Robert Schneider, Erie, CO (US);
Ralph E. Burns, Louisville, CO (US)

(73) Assignee: Arthrex, Inc., Naples, FL (US)

( * ) Notice: Subject to any disclaimer, the term of this patent is extended or adjusted under 35 U.S.C. 154(b) by 684 days.

(21) Appl. No.: 12/387,546

(22) Filed: May 4, 2009

(65) Prior Publication Data
US 2009/0287217 A1 Nov. 19, 2009

Related U.S. Application Data

(60) Division of application No. 11/396,490, filed on Apr. 3, 2006, which is a continuation-in-part of application No. 11/047,159, filed on Jan. 31, 2005, and a continuation-in-part of application No. 11/047,551, filed on Jan. 31, 2005, and a continuation-in-part of application No. 11/352,103, filed on Feb. 9, 2006, and a continuation-in-part of application No. 11/350,333, filed on Feb. 8, 2006.

(60) Provisional application No. 60/667,401, filed on Apr. 1, 2005, provisional application No. 60/736,135, filed on Nov. 10, 2005, provisional application No. 60/738,429, filed on Nov. 21, 2005, provisional application No. 60/741,313, filed on Dec. 1, 2005.

(51) Int. Cl.
*A61B 17/58* (2006.01)

(52) U.S. Cl.
USPC .................................. 606/88; 606/87; 606/90

(58) Field of Classification Search
USPC ................................................ 606/87, 90, 88
See application file for complete search history.

(56) References Cited

U.S. PATENT DOCUMENTS 2,737,724 A 3/1956 Herz
(Continued)

FOREIGN PATENT DOCUMENTS

CN 1132067 10/1996
(Continued)

OTHER PUBLICATIONS

Sohn, "Meniscus Transplantation: Current Concepts" The Journal of Knee Surgery, Apr. 2008, pp. 163-172, vol. 21, No. 2.
(Continued)

*Primary Examiner* — Thomas J Sweet
*Assistant Examiner* — Matthew Schall
(74) *Attorney, Agent, or Firm* — Dickstein Shapiro LLP

(57) ABSTRACT

Apparatus for performing an open wedge, high tibial osteotomy, the apparatus comprising:
cutting apparatus for forming an osteotomy cut in the tibia, the cutting apparatus comprising:
targeting apparatus for identifying a cutting plane through the tibia and a boundary line for terminating a cut made along the cutting plane, wherein the boundary line is located within the tibia, parallel to the anterior-posterior slope of the tibia and parallel to the sagittal plane of the patient.

A method for performing an open wedge, high tibial osteotomy, the method comprising:
positioning targeting apparatus for identifying a cutting plane through the tibia and a boundary line for terminating a cut made along the cutting plane, wherein the boundary line is located within the tibia, parallel to the anterior-posterior slope of the tibia and parallel to the sagittal plane of the patient;
cutting the bone along the cutting plane, with the cut terminating at the boundary line;
moving the bone on either side of the cut apart so as to form the wedge-like opening in the bone; and
stabilizing the bone.

10 Claims, 41 Drawing Sheets

LEFT LEG
ANTERIOR VIEW

(56) References Cited

U.S. PATENT DOCUMENTS

| | | | |
|---|---|---|---|
| 3,579,777 A | 5/1971 | Milewski | |
| 3,750,652 A | 8/1973 | Sherwin | |
| 4,335,715 A * | 6/1982 | Kirkley | 606/87 |
| 4,349,018 A * | 9/1982 | Chambers | 606/88 |
| 4,421,112 A * | 12/1983 | Mains et al. | 606/88 |
| 4,501,268 A | 2/1985 | Comparetto | |
| 4,523,587 A | 6/1985 | Frey | |
| 4,563,489 A | 1/1986 | Urist | |
| 4,565,191 A | 1/1986 | Slocum | |
| 4,750,481 A * | 6/1988 | Reese | 606/87 |
| 4,769,040 A | 9/1988 | Wevers | |
| 4,817,794 A | 4/1989 | Workman | |
| 4,851,005 A | 7/1989 | Hunt et al. | |
| 4,852,558 A | 8/1989 | Outerbridge | |
| 4,892,093 A | 1/1990 | Zarnowski et al. | |
| 4,936,844 A | 6/1990 | Chandler et al. | |
| 4,961,740 A | 10/1990 | Ray et al. | |
| 5,053,039 A | 10/1991 | Hoffmann et al. | |
| 5,254,119 A | 10/1993 | Schreiber | |
| 5,275,603 A | 1/1994 | Ferrante et al. | |
| 5,297,538 A | 3/1994 | Daniel | |
| 5,306,276 A | 4/1994 | Johnson et al. | |
| 5,352,229 A | 10/1994 | Goble et al. | |
| 5,413,579 A | 5/1995 | Tom Du Toit | |
| 5,445,640 A | 8/1995 | Johnson et al. | |
| 5,451,228 A | 9/1995 | Johnson et al. | |
| 5,540,695 A | 7/1996 | Levy | |
| 5,569,250 A | 10/1996 | Sarver et al. | |
| 5,601,565 A | 2/1997 | Huebner | |
| 5,609,635 A | 3/1997 | Michelson | |
| 5,613,969 A * | 3/1997 | Jenkins, Jr. | 606/87 |
| 5,620,448 A * | 4/1997 | Puddu | 606/87 |
| 5,640,813 A | 6/1997 | Glazik et al. | |
| 5,662,655 A | 9/1997 | Laboureau et al. | |
| 5,669,909 A | 9/1997 | Zdeblick et al. | |
| 5,674,296 A | 10/1997 | Bryan et al. | |
| 5,681,316 A | 10/1997 | DeOrio et al. | |
| H1706 H * | 1/1998 | Mason | 606/87 |
| 5,722,978 A * | 3/1998 | Jenkins, Jr. | 606/87 |
| 5,733,290 A | 3/1998 | McCue et al. | |
| 5,749,875 A * | 5/1998 | Puddu | 606/87 |
| 5,766,251 A * | 6/1998 | Koshino | 623/11.11 |
| 5,843,085 A | 12/1998 | Graser | |
| 5,888,223 A | 3/1999 | Bray, Jr. | |
| 5,911,724 A | 6/1999 | Wehril | |
| 5,928,231 A * | 7/1999 | Klein et al. | 606/60 |
| 5,980,526 A * | 11/1999 | Johnson et al. | 606/86 R |
| 6,008,433 A | 12/1999 | Stone | |
| 6,027,504 A * | 2/2000 | McGuire | 606/87 |
| 6,039,761 A | 3/2000 | Li et al. | |
| 6,086,593 A | 7/2000 | Bonutti | |
| 6,099,531 A | 8/2000 | Bonutti | |
| 6,102,950 A | 8/2000 | Vaccaro | |
| 6,171,307 B1 * | 1/2001 | Orlich | 606/53 |
| 6,190,390 B1 | 2/2001 | McAllister | |
| 6,200,347 B1 | 3/2001 | Anderson et al. | |
| 6,203,546 B1 | 3/2001 | MacMahon | |
| 6,214,007 B1 | 4/2001 | Anderson | |
| 6,224,599 B1 | 5/2001 | Baynham et al. | |
| 6,264,694 B1 | 7/2001 | Weiler | |
| 6,277,149 B1 | 8/2001 | Boyle et al. | |
| 6,287,308 B1 | 9/2001 | Betz et al. | |
| 6,379,361 B1 | 4/2002 | Beck, Jr. et al. | |
| 6,423,063 B1 | 7/2002 | Bonutti | |
| 6,461,359 B1 | 10/2002 | Tribus et al. | |
| 6,478,800 B1 | 11/2002 | Fraser et al. | |
| 6,544,266 B1 * | 4/2003 | Roger et al. | 606/70 |
| 6,565,570 B2 | 5/2003 | Sterett et al. | |
| 6,575,982 B1 | 6/2003 | Bonutti | |
| 6,699,252 B2 | 3/2004 | Farr, II et al. | |
| 6,743,255 B2 | 6/2004 | Ferree | |
| 6,755,841 B2 | 6/2004 | Fraser et al. | |
| 6,796,986 B2 | 9/2004 | Duffner | |
| 6,823,871 B2 * | 11/2004 | Schmieding | 128/898 |
| 7,001,385 B2 * | 2/2006 | Bonutti | 606/60 |
| 7,018,383 B2 * | 3/2006 | McGuire | 606/102 |
| 7,510,557 B1 * | 3/2009 | Bonutti | 606/86 R |
| 7,875,033 B2 * | 1/2011 | Richter et al. | 606/90 |
| 7,879,109 B2 * | 2/2011 | Borden et al. | 623/23.76 |
| 2001/0029375 A1 * | 10/2001 | Betz et al. | 606/61 |
| 2002/0010513 A1 | 1/2002 | Schmieding | |
| 2002/0029084 A1 | 3/2002 | Paul et al. | |
| 2002/0095156 A1 | 7/2002 | Kuras et al. | |
| 2003/0028196 A1 * | 2/2003 | Bonutti | 606/87 |
| 2003/0028197 A1 | 2/2003 | Hanson et al. | |
| 2003/0105526 A1 * | 6/2003 | Bryant et al. | 623/16.11 |
| 2003/0171757 A1 | 9/2003 | Coon et al. | |
| 2003/0191475 A1 * | 10/2003 | McGuire | 606/102 |
| 2003/0195516 A1 * | 10/2003 | Sterett et al. | 606/69 |
| 2003/0199881 A1 | 10/2003 | Bonutti | |
| 2004/0039387 A1 | 2/2004 | Gause et al. | |
| 2004/0172028 A1 * | 9/2004 | Roger | 606/69 |
| 2004/0249377 A1 | 12/2004 | Kaes et al. | |
| 2005/0075641 A1 | 4/2005 | Singhatat et al. | 606/86 |
| 2005/0177245 A1 * | 8/2005 | Leatherbury et al. | 623/23.5 |
| 2005/0187559 A1 * | 8/2005 | Raymond et al. | 606/90 |
| 2005/0216090 A1 | 9/2005 | O'Driscoll et al. | |
| 2005/0228498 A1 | 10/2005 | Andres | |
| 2005/0234448 A1 * | 10/2005 | McCarthy | 606/57 |
| 2005/0251147 A1 * | 11/2005 | Novak | 606/87 |
| 2005/0273114 A1 * | 12/2005 | Novak | 606/88 |
| 2005/0273115 A1 | 12/2005 | Coon et al. | |
| 2006/0015118 A1 * | 1/2006 | Richter et al. | 606/90 |
| 2006/0106396 A1 | 5/2006 | Justin et al. | |
| 2006/0122617 A1 | 6/2006 | Lavallee et al. | |
| 2006/0129163 A1 | 6/2006 | McGuire | |
| 2006/0149274 A1 | 7/2006 | Justin et al. | |
| 2006/0149275 A1 | 7/2006 | Cadmus | |
| 2006/0217808 A1 | 9/2006 | Novak et al. | |
| 2006/0229629 A1 * | 10/2006 | Manzi et al. | 606/90 |
| 2006/0241636 A1 | 10/2006 | Novak et al. | |

FOREIGN PATENT DOCUMENTS

| | | |
|---|---|---|
| CN | 1181696 | 5/1998 |
| EP | 1 099 428 | 5/2001 |
| EP | 1669033 | 6/2006 |
| FR | 2741525 | 5/1997 |
| FR | 2 764 183 | 12/1998 |
| WO | WO 96/14802 | 5/1996 |
| WO | WO 99/52473 | 10/1999 |
| WO | WO 2005/048888 | 6/2005 |
| WO | WO 2006/107800 | 10/2006 |

OTHER PUBLICATIONS

Oliver C. Kessler et al., "Avoidance of Medial Cortical Fracture in High Tibial Osteotomy: Improved Technique," Clinical Orthopaedics and Related Research, Feb. 2002, pp. 180-185, No. 395.

* cited by examiner

TOP VIEW

LATERAL VIEW UNDER FLUOROSCOPY, WITH GUIDE ELEMENT NOT VERTICALLY ALIGNED WITH FLUOROSCOPE

LATERAL VIEW UNDER FLUOROSCOPY, WITH GUIDE ELEMENT VERTICALLY ALIGNED WITH FLUOROSCOPE

METHOD AND APPARATUS FOR PERFORMING AN OPEN WEDGE, HIGH TIBIAL OSTEOTOMY

REFERENCE TO PENDING PRIOR PATENT APPLICATIONS

This patent application is a division of prior U.S. patent application Ser. No. 11/396,490, filed Apr. 3, 2006 by Kelly Ammann et al. for METHOD AND APPARATUS FOR PERFORMING AN OPEN WEDGE, HIGH TIBIAL OSTEOTOMY, which in turn:

(i) is a continuation-in-part of pending prior U.S. patent application Ser. No. 11/047,159, filed Jan. 31, 2005 by Vincent P. Novak for OPEN WEDGE OSTEOTOMY SYSTEM AND SURGICAL METHOD;

(ii) is a continuation-in-part of pending prior U.S. patent application Ser. No. 11/047,551, filed Jan. 31, 2005 by Vincent P. Novak for OPEN WEDGE OSTEOTOMY SYSTEM AND SURGICAL METHOD;

(iii) is a continuation-in-part of pending prior U.S. patent application Ser. No. 11/352,103, filed Feb. 09, 2006 by Vincent P. Novak et al. for MULTI-PART IMPLANT FOR OPEN WEDGE KNEE OSTEOTOMIES;

(iv) is a continuation-in-part of pending prior U.S. patent application Ser. No. 11/350,333, filed Feb. 08, 2006 by Vincent P. Novak et al. for METHOD AND APPARATUS FOR FORMING A WEDGE-LIKE OPENING IN A BONE FOR AN OPEN WEDGE OSTEOTOMY;

(v) claims benefit of prior U.S. Provisional Patent Application Ser. No. 60/667,401, filed Apr. 1, 2005 by Kelly Anmann et al. for OPEN WEDGE OSTEOTOMY SYSTEM AND SURGICAL METHOD;

(vi) claims benefit of prior U.S. Provisional Patent Application Ser. No. 60/736,135, filed Nov. 10, 2005 by Kelly Anmann et al. for DESCRIPTION OF A METHOD FOR OBTAINING AN ANTERIOR TO POSTERIOR (AP) SLOPE CORRECTION IN CONJUNCTION WITH A LATERAL TO MEDIAL (LM) CORRECTION USING HIGH TIBIAL OSTEOTOMY;

(vii) claims benefit of prior U.S. Provisional Patent Application Ser. No. 60/738,429, filed Nov. 21, 2005 by Vincent P. Novak et al. for METHOD AND SYSTEM OF INSTRUMENTATION FOR PERFORMING AN OPENING WEDGE OSTEOTOMY; and (viii) claims benefit of prior U.S. Provisional Patent Application Ser. No. 60/741,313, filed Dec. 1, 2005 by Kelly Ammann et al. for METHOD AND SYSTEM OF FIXATION FOR PERFORMING AN OPENING WEDGE OSTEOTOMY.

The above-identified patent applications are hereby incorporated herein by reference.

FIELD OF THE INVENTION

This invention relates to surgical methods and apparatus in general, and more particularly to surgical methods and apparatus for performing open wedge osteotomies of the knee.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to the relatively unaffected portions of the joint.

Knee osteotomies are also an important technique for addressing abnormal knee geometries, e.g., due to birth defect, injury, etc.

Most knee osteotomies are designed to modify the geometry of the tibia, so as to adjust the manner in which the load is transferred across the knee joint.

There are essentially two ways in which to adjust the orientation of the tibia: (i) the closed wedge technique; and (ii) the open wedge technique.

With the closed wedge technique, a wedge of bone is removed from the upper portion of the tibia, and then the tibia manipulated so as to close the resulting gap, whereby to reorient the lower portion of the tibia relative to the tibial plateau and hence adjust the manner in which load is transferred from the femur to the tibia.

With the open wedge technique, a cut is made into the upper portion of the tibia, the tibia is manipulated so as to open a wedge-like opening in the bone, and then the bone is secured in this position (e.g., by screwing metal plates to the bone or by inserting a wedge-shaped implant into the opening in the bone), whereby to reorient the lower portion of the tibia relative to the tibial plateau and hence adjust the manner in which load is transferred from the femur to the tibia.

While both closed wedge osteotomies and open wedge osteotomies provide substantial benefits to the patient, they are procedurally challenging for the surgeon. Among other things, with respect to open wedge osteotomies, it can be difficult to create the wedge-like opening in the bone with the necessary precision and with a minimum of trauma to the surrounding tissue.

The present invention is directed to open wedge osteotomies of the knee.

SUMMARY OF THE INVENTION

The present invention comprises a novel method and apparatus for performing an open wedge, high tibial osteotomy. More particularly, the present invention comprises the provision and use of a novel method and apparatus for forming an appropriate osteotomy cut into the upper portion of the tibia, manipulating the tibia so as to open an appropriate wedge-like opening in the tibia, and then inserting an appropriate wedge-shaped implant into the wedge-like opening in the tibia, so as to stabilize the tibia with the desired orientation, whereby to reorient the lower portion of the tibia relative to the tibial plateau and hence adjust the manner in which load is transferred from the femur to the tibia.

In one form of the present invention, there is provided apparatus for performing an open wedge, high tibial osteotomy, the apparatus comprising:

cutting apparatus for forming an osteotomy cut in the tibia, the cutting apparatus comprising:
targeting apparatus for identifying a cutting plane through the tibia and a boundary line for terminating a cut made along the cutting plane, wherein the boundary line is located within the tibia, parallel to the anterior-posterior slope of the tibia and parallel to the sagittal plane of the patient.

In another form of the invention, there is provided a method for performing an open wedge, high tibial osteotomy, the method comprising:

positioning targeting apparatus for identifying a cutting plane through the tibia and a boundary line for terminating a cut made along the cutting plane, wherein the boundary line is located within the tibia, parallel to the anterior-posterior slope of the tibia and parallel to the sagittal plane of the patient;

cutting the bone along the cutting plane, with the cut terminating at the boundary line;

moving the bone on either side of the cut apart so as to form the wedge-like opening in the bone; and stabilizing the bone.

In another form of the invention, there is provided apparatus for performing an open wedge, high tibial osteotomy, the apparatus comprising:

a wedge-shaped implant for disposition in a wedge-shaped opening created in the tibia, wherein the wedge-shaped implant comprises at least one key for disposition in a keyhole formed in the tibia adjacent to the wedge-shaped opening created in the tibia.

In another form of the invention, there is provided a method for performing an open wedge, high tibial osteotomy, the method comprising:

cutting the bone along a cutting plane, with the cut terminating at a boundary line, and forming at least one keyhole in the tibia adjacent to the cut;

moving the bone on either side of the cut apart so as to form a wedge-like opening in the bone; and positioning a wedge-shaped implant in the wedge-shaped opening created in the tibia, wherein the wedge-shaped implant comprises at least one key, and further wherein the at least one key is disposed in the at least one keyhole formed in the tibia.

In another form of the invention, there is provided apparatus for performing an open wedge, high tibial osteotomy, the apparatus comprising:

cutting apparatus for forming an osteotomy cut in the tibia, the cutting apparatus comprising:

targeting apparatus for identifying a cutting plane through the tibia and a boundary line for terminating a cut made along the cutting plane, wherein the boundary line is located within the tibia, parallel to the anterior-posterior slope of the tibia and at a selected angle to the sagittal plane of the patient.

In another form of the invention, there is provided a method for performing an open wedge, high tibial osteotomy, the method comprising:

positioning targeting apparatus for identifying a cutting plane through the tibia and a boundary line for terminating a cut made along the cutting plane, wherein the boundary line is located within the tibia, parallel to the anterior-posterior slope of the tibia and at a selected angle to the sagittal plane of the patient;

cutting the bone along the cutting plane, with the cut terminating at the boundary line;

moving the bone on either side of the cut apart so as to form the wedge-like opening in the bone; and stabilizing the bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Overview of an Open Wedge, High Tibial Osteotomy

Figure 1:
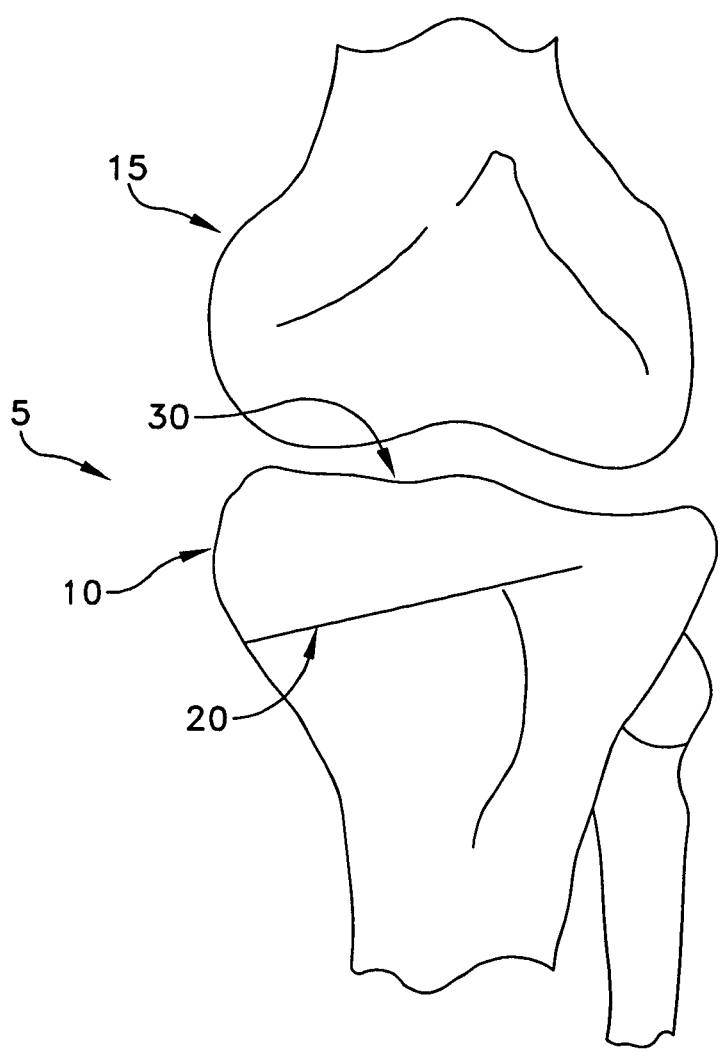
FIGS. 1-3 are schematic views showing the formation of a wedge-like opening in the tibia for an open wedge, high tibial osteotomy, and positioning of a wedge-shaped implant into the wedge-like opening in the tibia.
Figure 2:
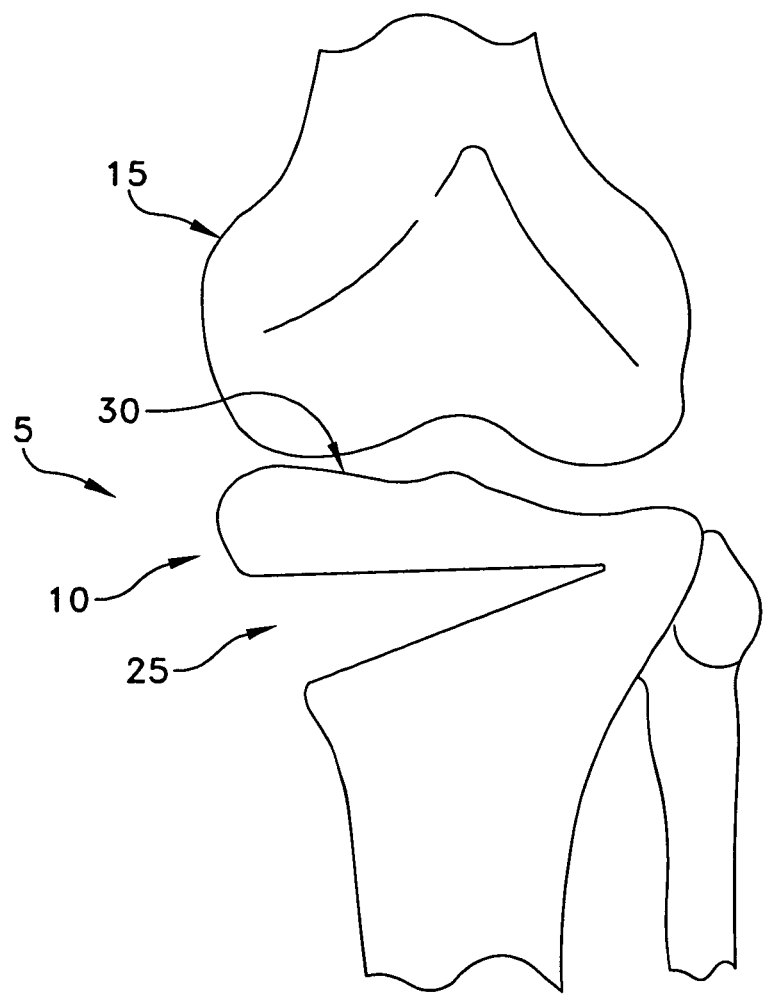
Figure 3:
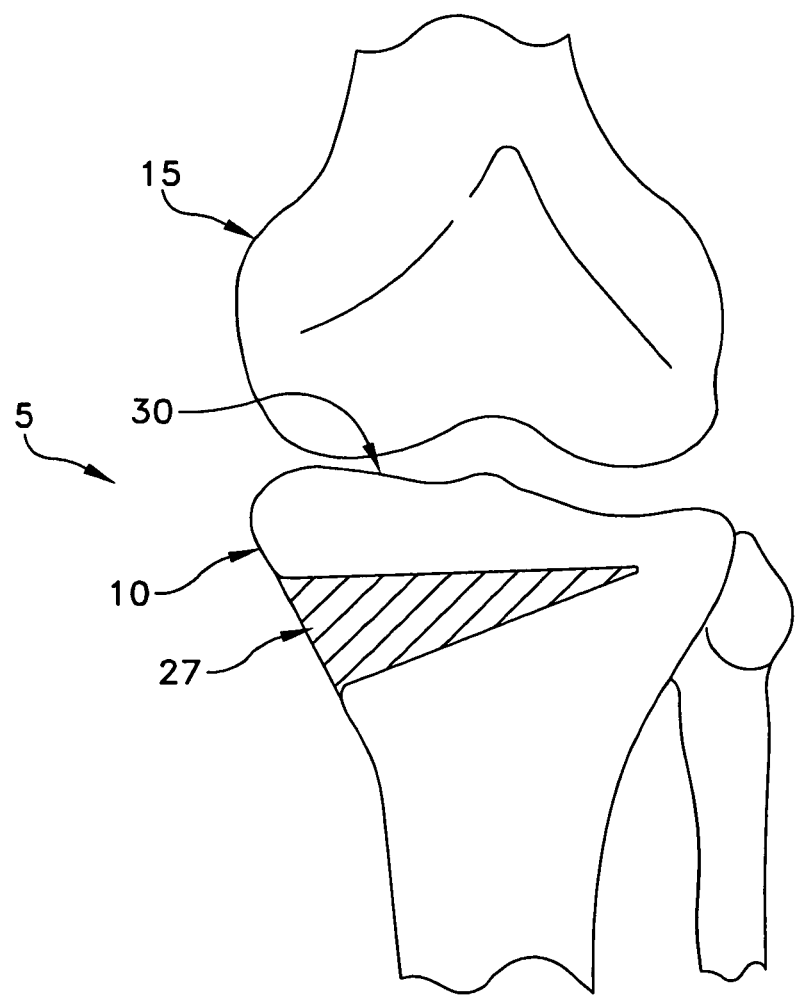

Looking first at FIGS. 1-3, there is shown a knee joint 5 upon which an open wedge osteotomy is to be performed. Knee joint 5 generally comprises a tibia 10 and a femur 15. In accordance with the present invention, the open wedge osteotomy is effected by first making a cut 20 (FIG. 1) into the upper tibia, and then manipulating the lower portion of the tibia so as to open a wedge-like opening 25 (FIG. 2) in the bone, with the wedge-like opening 25 being configured so as to adjust the manner in which load is transferred from the femur to the tibia. Cut 20 and wedge-like opening 25 may be formed in a variety of ways well known in the art.

Among other things, the present invention provides a new and improved method and apparatus for forming cut 20 and wedge-like opening 25, as will be discussed in detail below.

Once the desired wedge-like opening 25 has been formed in tibia 10 so as to reconfigure tibia 10 to the desired geometry, the bone may be secured in position in a variety of ways well known in the art (e.g., by screwing metal plates to the bone or by inserting a wedge-shaped implant into the opening in the bone), whereby to adjust the manner in which load is transferred from the femur to the tibia. By way of example, FIG. 3 shows a wedge-shaped implant 27 inserted into the wedge-like opening 25 formed in the tibia, whereby to stabilize the tibia in its reconfigured geometry.

Among other things, the present invention also provides a new and improved wedge-shaped implant, and an associated method and apparatus for deploying the same into the wedge-shaped opening in the tibia.

Figure 3A:
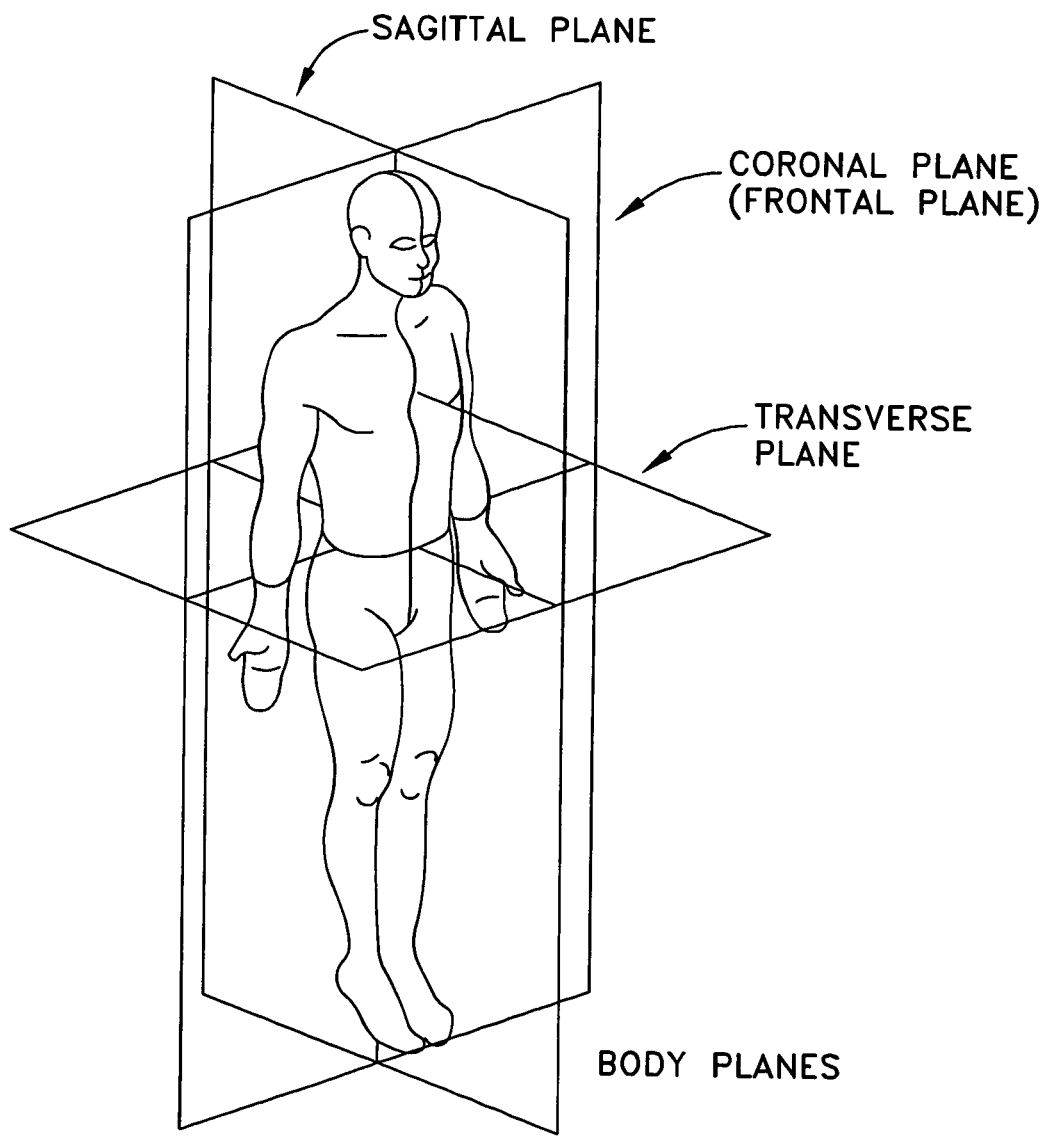
FIG. 3A is a schematic view showing selected anatomical planes.

Discussion of the Relevant Planar Surfaces in the High Tibial Osteotomy of the Present Invention In order to appreciate certain aspects of the present invention, it is helpful to have a thorough understanding of the planar surfaces of the tibia that are relevant in performing the high tibial osteotomy of the present invention. Thus, the following discussion presents a geometric description of the planar surfaces that are relevant to the open wedge, high tibial osteotomy of the present invention. For the purposes of the present discussion, it can sometimes be helpful to make reference to selected anatomical planes, e.g., the coronal plane, the sagittal plane and the transverse plane (FIG. 3A).

Figure 4:
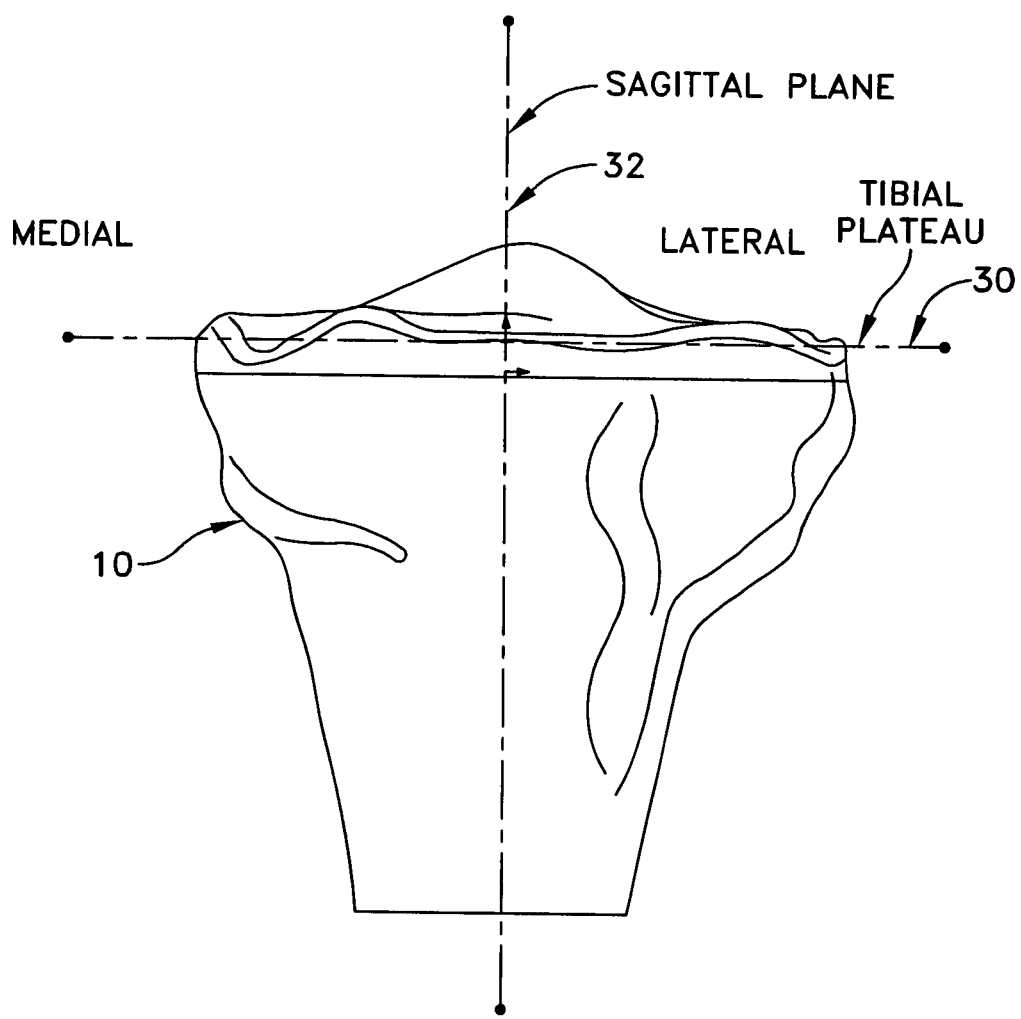
FIGS. 4-9 show the relevant planar surfaces in an open wedge, high tibial osteotomy.
Figure 5:
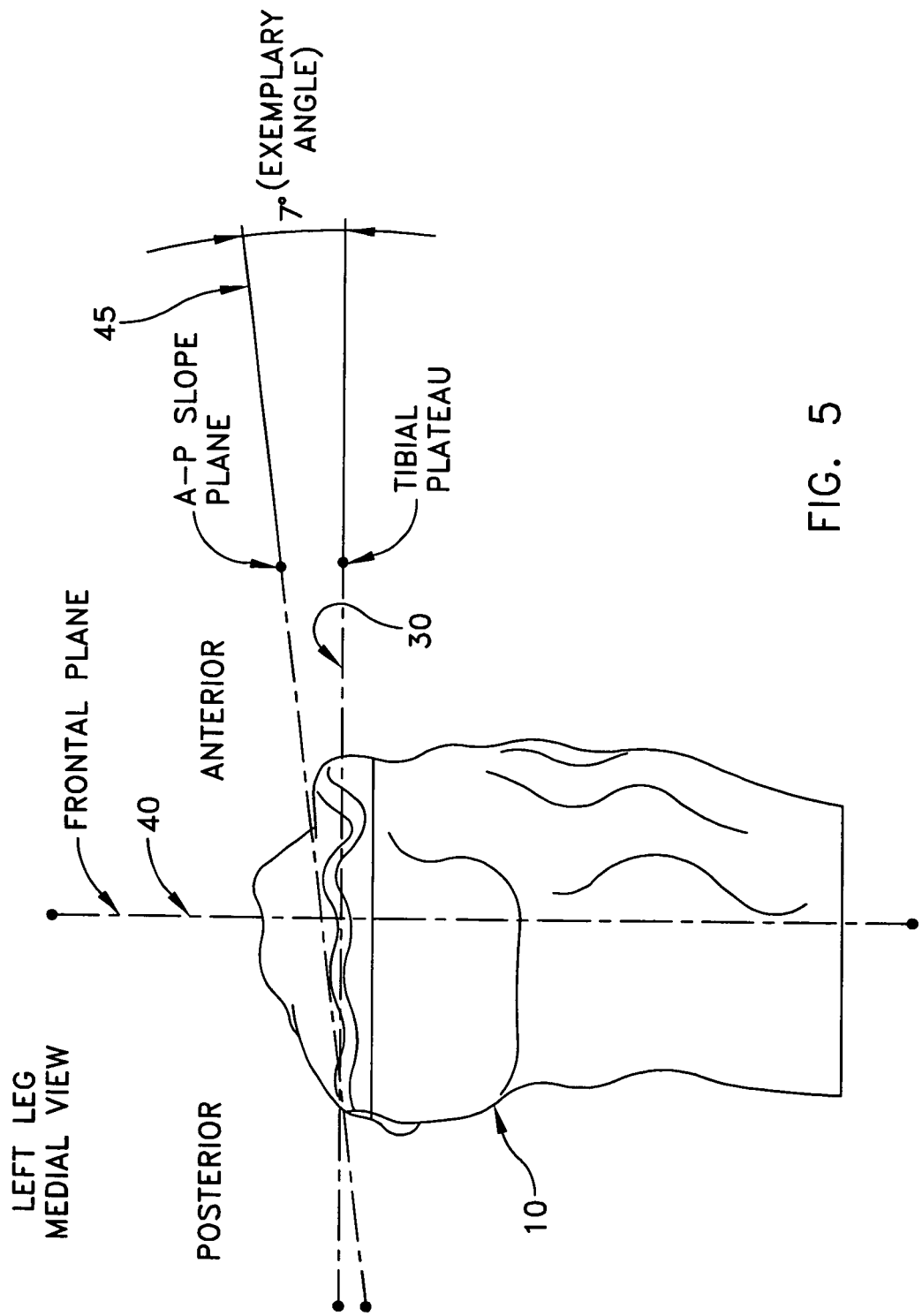

Looking now at FIGS. 1-4, for the purposes of the present invention, the tibial plateau 30 may be described as a horizontal (or transverse) plane that extends along the superior surface of tibia 10. For reference, the sagittal plane 32 is also shown in FIG. 4. As seen in FIG. 5, tibial plateau 30 is also perpendicular to the frontal (or coronal) plane 40. The anterior-posterior (A-P) slope is defined by an anterior-posterior (A-P) slope plane 45 that extends along the sloping top surface of the tibia from anterior-to-posterior. Published research has demonstrated that the anterior-posterior (A-P) slope typically extends at an angle of approximately 7° to 11° to the tibial plateau 30; however, the specific angle may vary from individual to individual.

Figure 6:
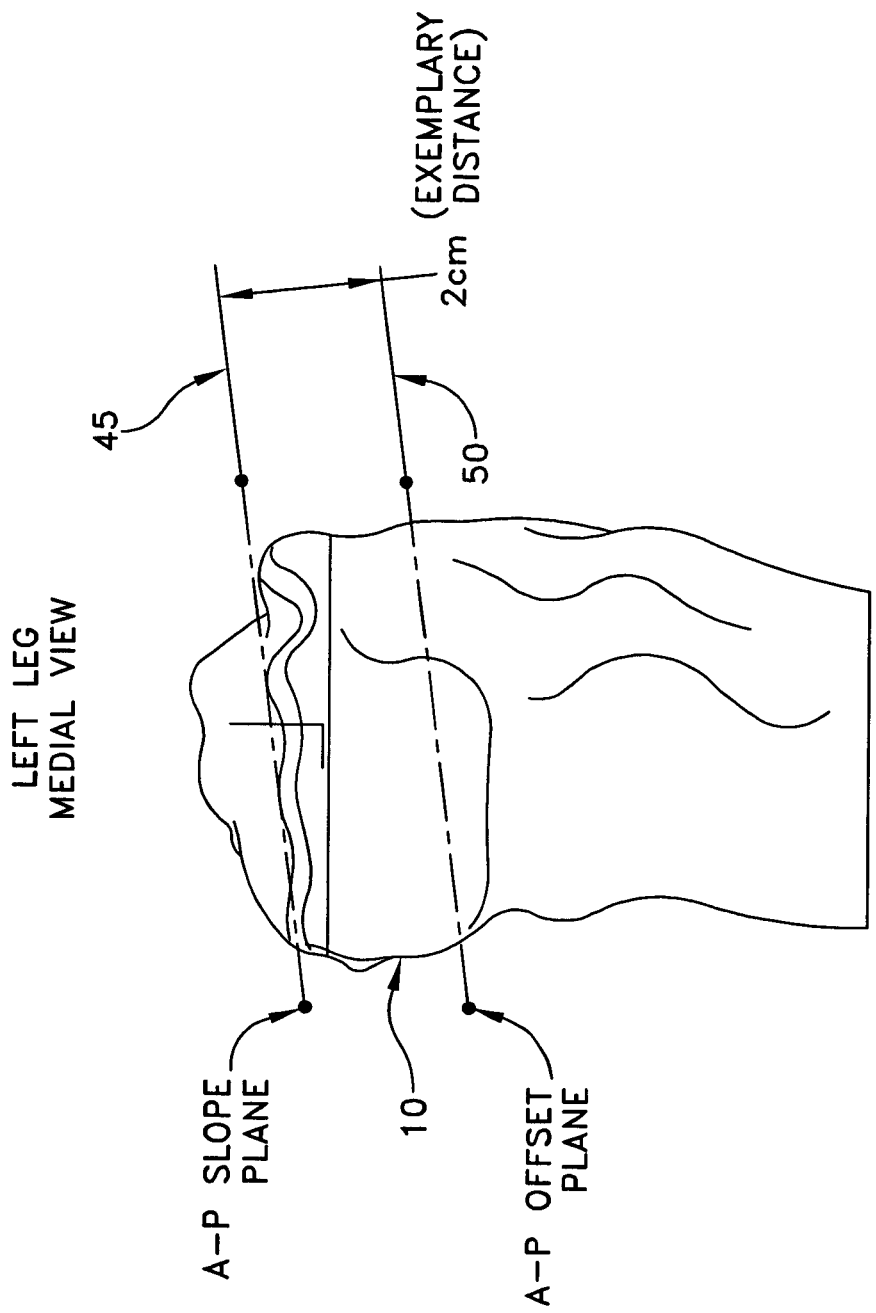

Looking next at FIG. 6, for the high tibial osteotomy of the present invention, it is generally desirable to stay about 2 cm inferior to the A-P slope plane 45. This offset can be referred to as the A-P offset plane 50.

Figure 7:
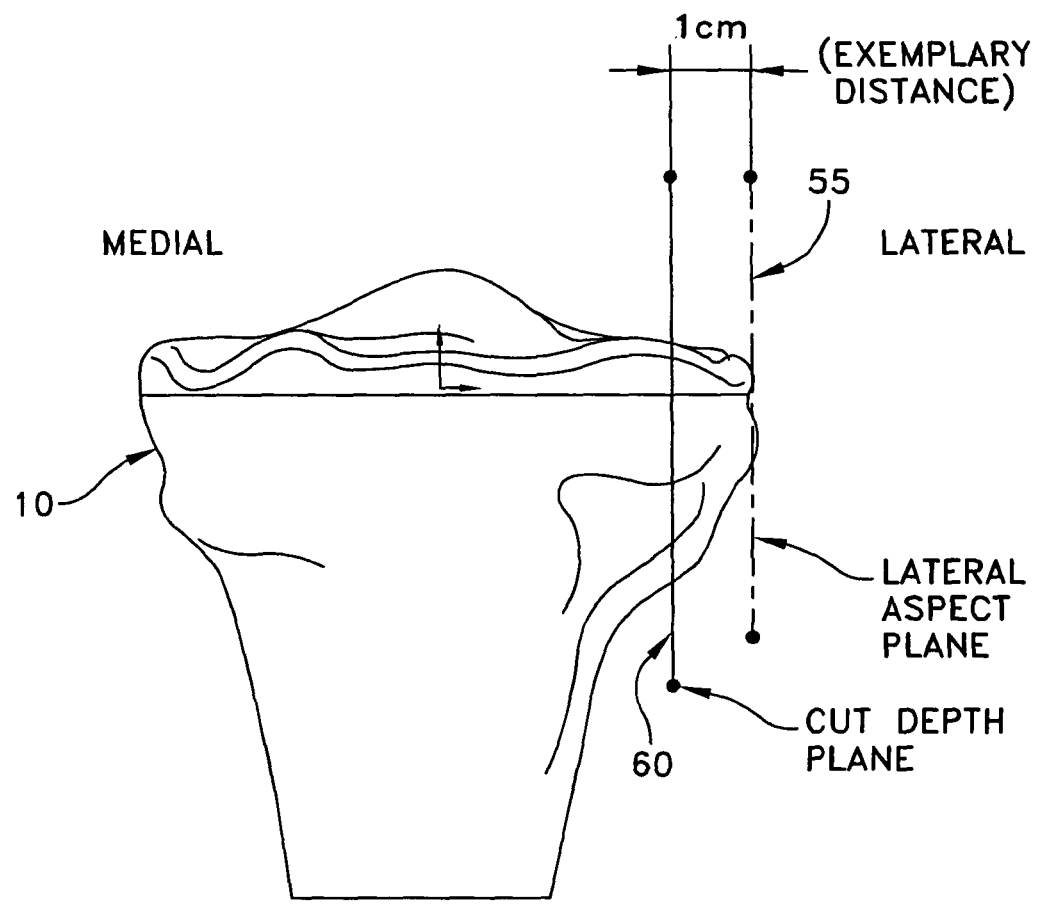

As seen in FIG. 7, the lateral aspect and cut depth may be defined by a lateral aspect plane 55 and a cut depth plane 60, with the cut depth being about 1 cm medial to the lateral aspect of the tibia.

Figure 8:
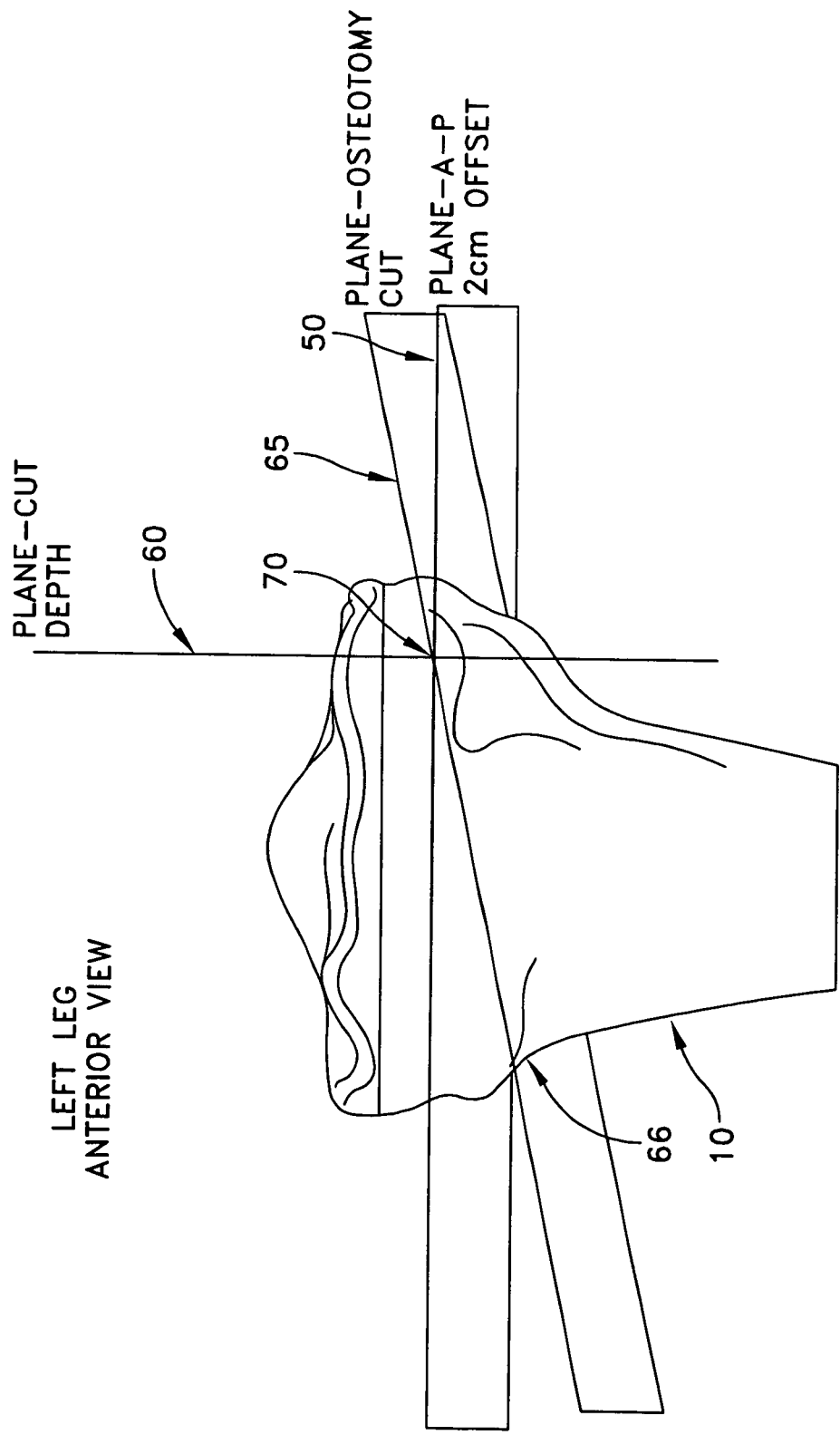

Looking next at FIG. 8, the osteotomy cut plane 65 (when seen from the direct frontal view of FIG. 8) is formed by a plane that is rotated away from the A-P offset plane 50 through an axis formed by the intersection of the cut depth plane 60 and the A-P offset plane 50. The degree of rotation is selected so as to be sufficient to place the entry of the osteotomy cut plane 65 at the medial neck 66 (FIG. 8) of the tibia. It should be noted that the A-P offset plane 50 and the osteotomy cut plane 65 are "tilted" slightly from anterior to posterior (but not seen in the direct frontal view of FIG. 8), since the A-P offset plane 50 and the osteotomy cut plane 65 follow the tilt of the A-P slope plane 45 (FIG. 6). The intersection of the A-P offset plane 50 and the cut depth plane 60 forms an axis 70 which, in accordance with the present invention, defines the lateral limit of the osteotomy cut. In other words, axis 70 defines a line through the tibia which is (i) parallel to A-P slope plane 45, and (ii) contained within osteotomy cut plane 65. Furthermore, in accordance with the present invention, axis 70 is used to define the lateral limit of the osteotomy cut which is to be made into the tibia.

Figure 9:
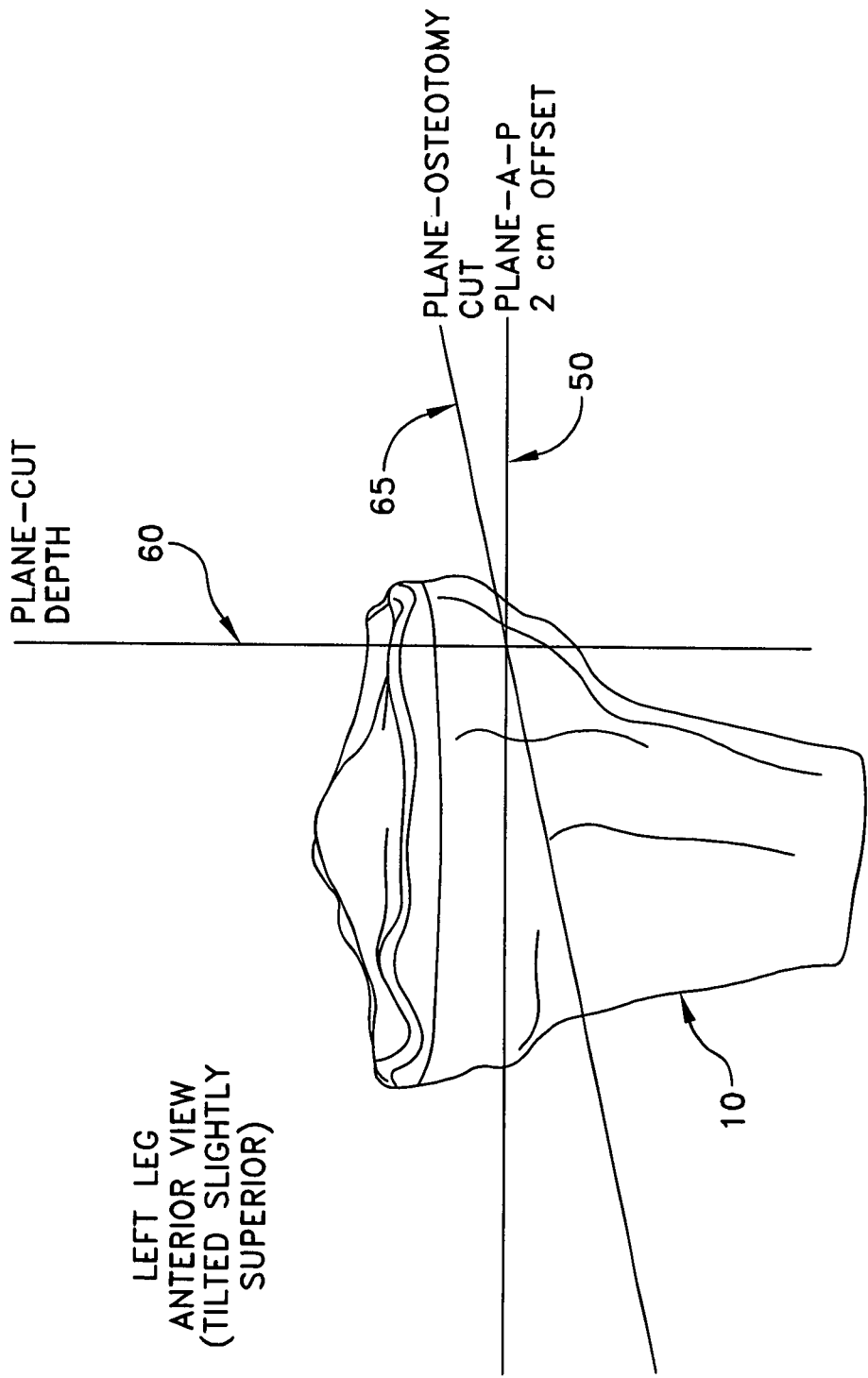

As seen in FIG. 9, the direct view of the osteotomy plane is a direct view in line with the osteotomy. This view is tilted downward (e.g., at approximately 7°) from the direct frontal view. Again, the angle of tilt downward is equal to the A-P slope. In other words, with the present invention, the osteotomy cut plane 65 extends parallel to the A-P slope plane 45 (in the anterior-to-posterior direction, although not in the medial-to-lateral direction), and typically slopes downward (e.g., at an angle of 7-11°) when viewed in the anterior-to-posterior direction. Furthermore, with the present invention, the axis 70 (which defines the lateral limit to the osteotomy cut) is contained within the osteotomy cut plane 65.

Figure 18:
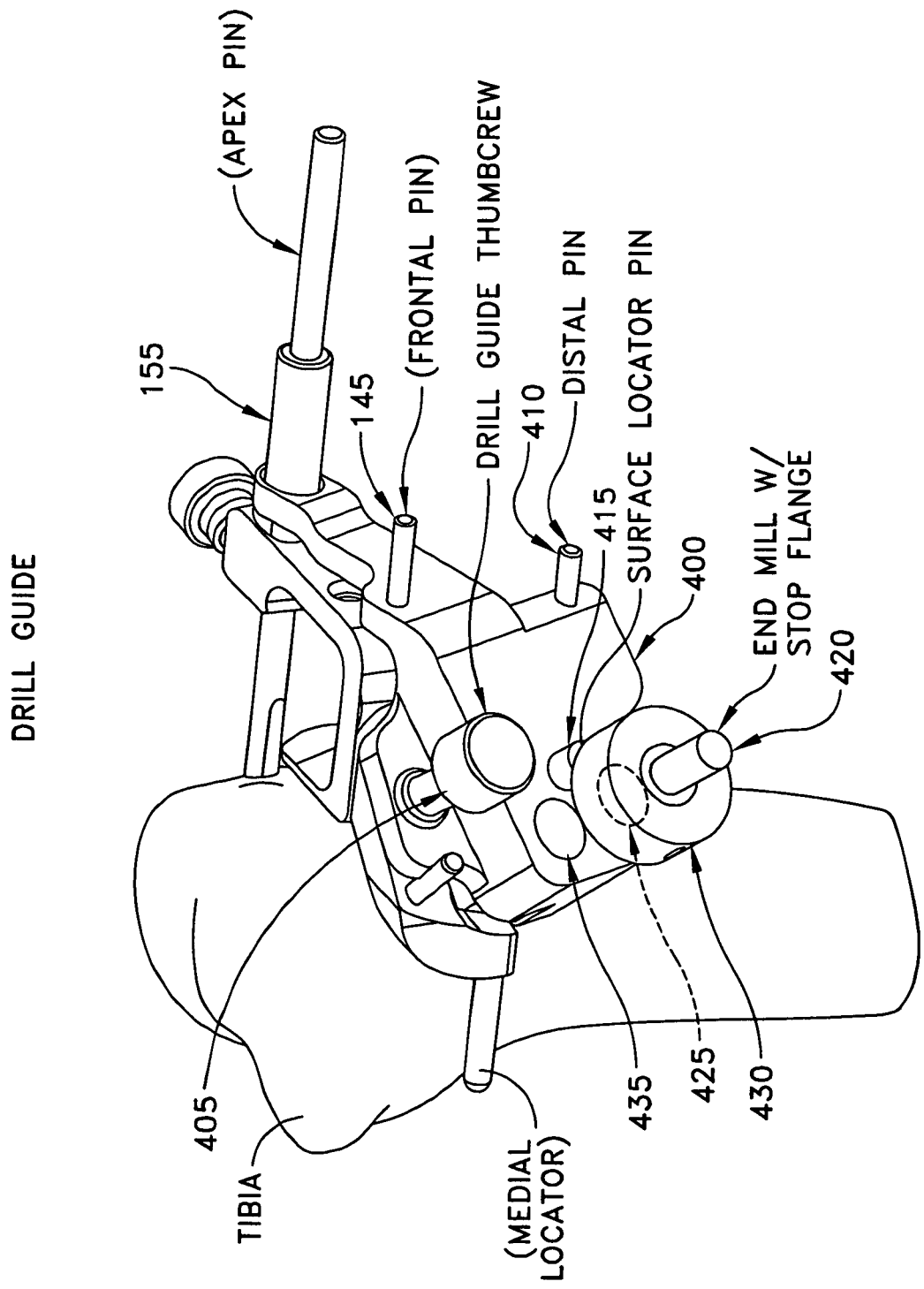

Novel Method and Apparatus for Performing the Open Wedge, High Tibial Osteotomy of the Present Invention In one preferred embodiment of the present invention, there is provided a novel osteotomy system which comprises instrumentation for use in making precise and repeatable osteotomy cuts for use in open wedge, high tibial osteotomies, preferably using an antero-medial approach. The novel osteotomy system generally comprises a positioning guide 100 (FIG. 16), a slope guide 200 (FIG. 11), an apex pin 300 (FIG. 16), a keyhole drill guide 400 (FIG. 18), a posterior protector 500 (FIG. 20), and a cutting guide 600 (FIG. 20), as will hereinafter be discussed in further detail.

Figure 22:
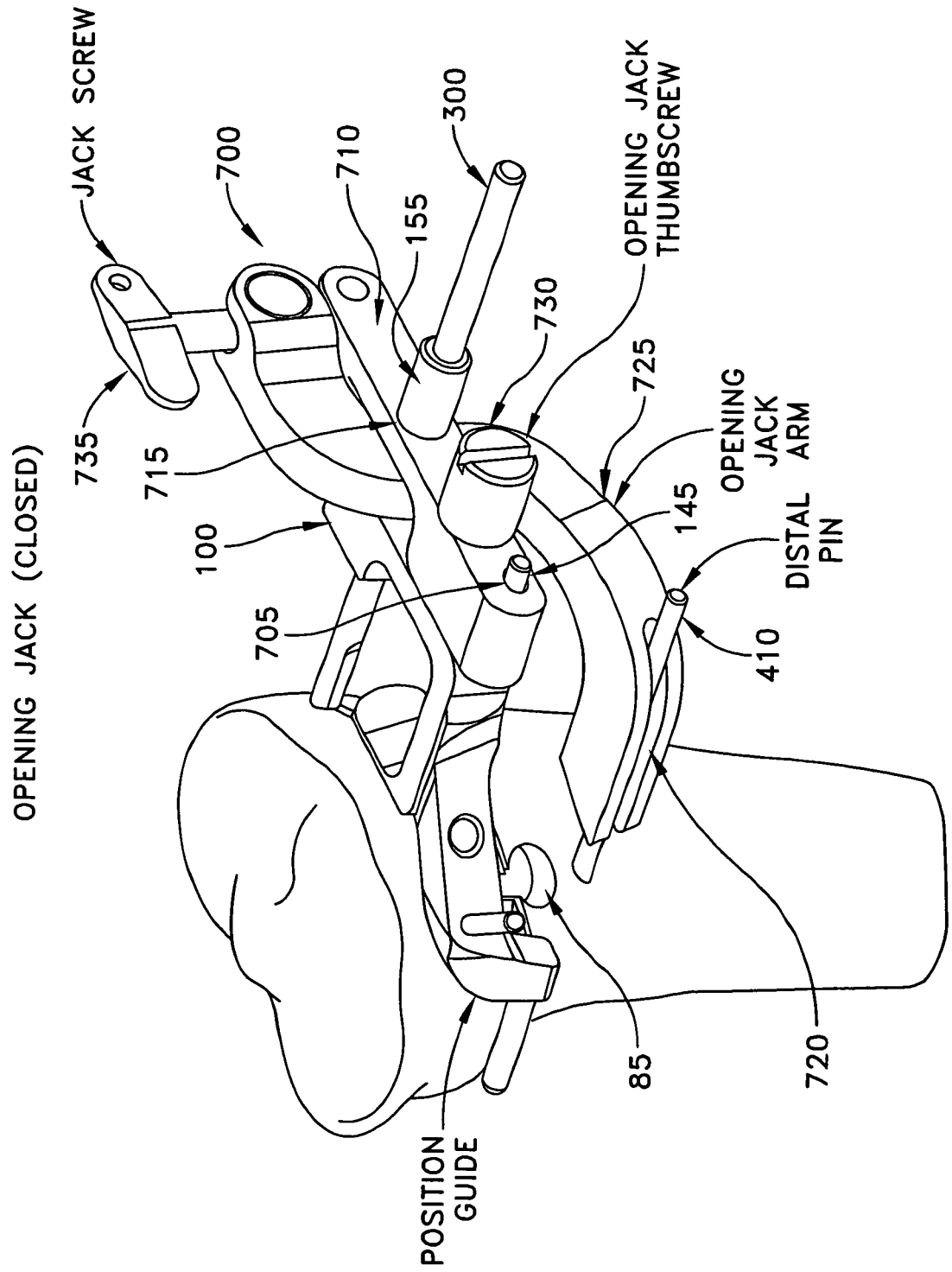

The novel osteotomy system preferably also comprises a novel opening jack 700 (FIG. 22) for opening the cut in the tibia so as to form the wedge-like opening in the tibia, as will also hereinafter be discussed in further detail.

Figure 24:
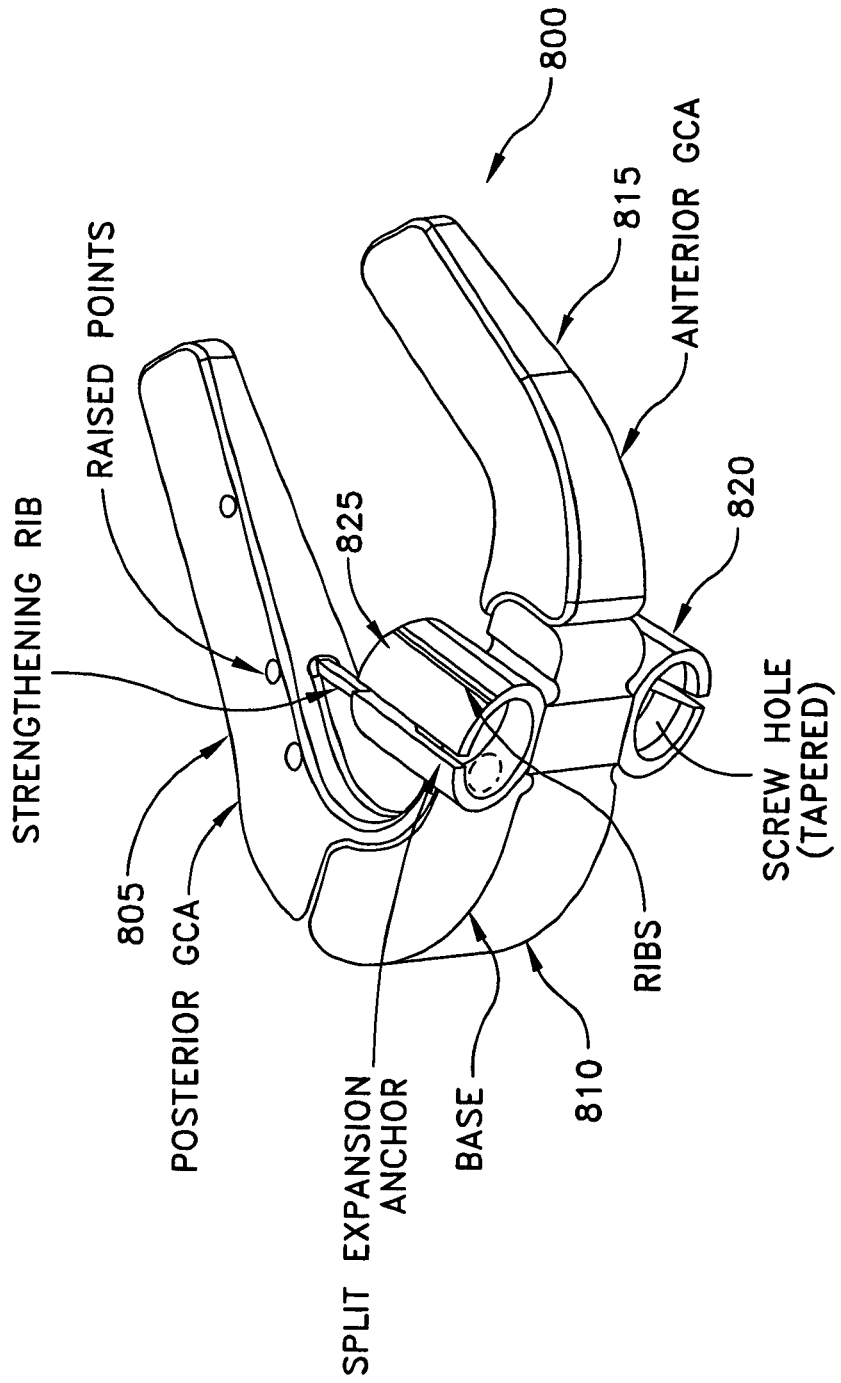

And the novel osteotomy system preferably also includes a novel implant 800 (FIG. 24) for positioning in the wedge-like opening in the tibia so as to stabilize the tibia in its corrected configuration, as will also hereinafter be discussed in further detail.

In a preferred form of the invention, the novel osteotomy system is configured so that:

(i) the axis 70 formed at the lateral limit of the osteotomy cut (which forms the lateral bony hinge when the osteotomy cut is opened) is parallel to the A-P tibial slope;

(ii) the axis of the lateral bony hinge created by the osteotomy lies in a plane that is perpendicular to the frontal (i.e., coronal) plane; and (iii) when the osteotomy is completed and the wedge is opened, the distal (i.e., lower) tibia is rotated about the bony hinge so as to substantially maintain, in anatomical alignment, the A-P slope and the frontal plane.

In a preferred form of the invention, the novel osteotomy system is also configured so that:

(iv) the osteotomy can be performed less invasively; and (v) the osteotomy can be performed with minimum incising of soft tissue such as the medial collateral ligament, the lateral collateral ligament, and the hamstrings.

In one preferred form of the invention, the novel osteotomy system is constructed and used as follows.

1. A vertical incision is first made on the antero-medial portion of the knee, approximately 1 cm from the medial edge of the patellar tendon, with the incision beginning approximately 2.5-3 cm inferior to the joint line, and extending approximately 6-10 cm in length.

2. The soft tissue between the patellar tendon and the proximal tibia surface is then dissected in order to make a small tunnel-like opening beneath the patellar tendon, just above the patellar tendon's insertion to the proximal tibia.

Figure 10:
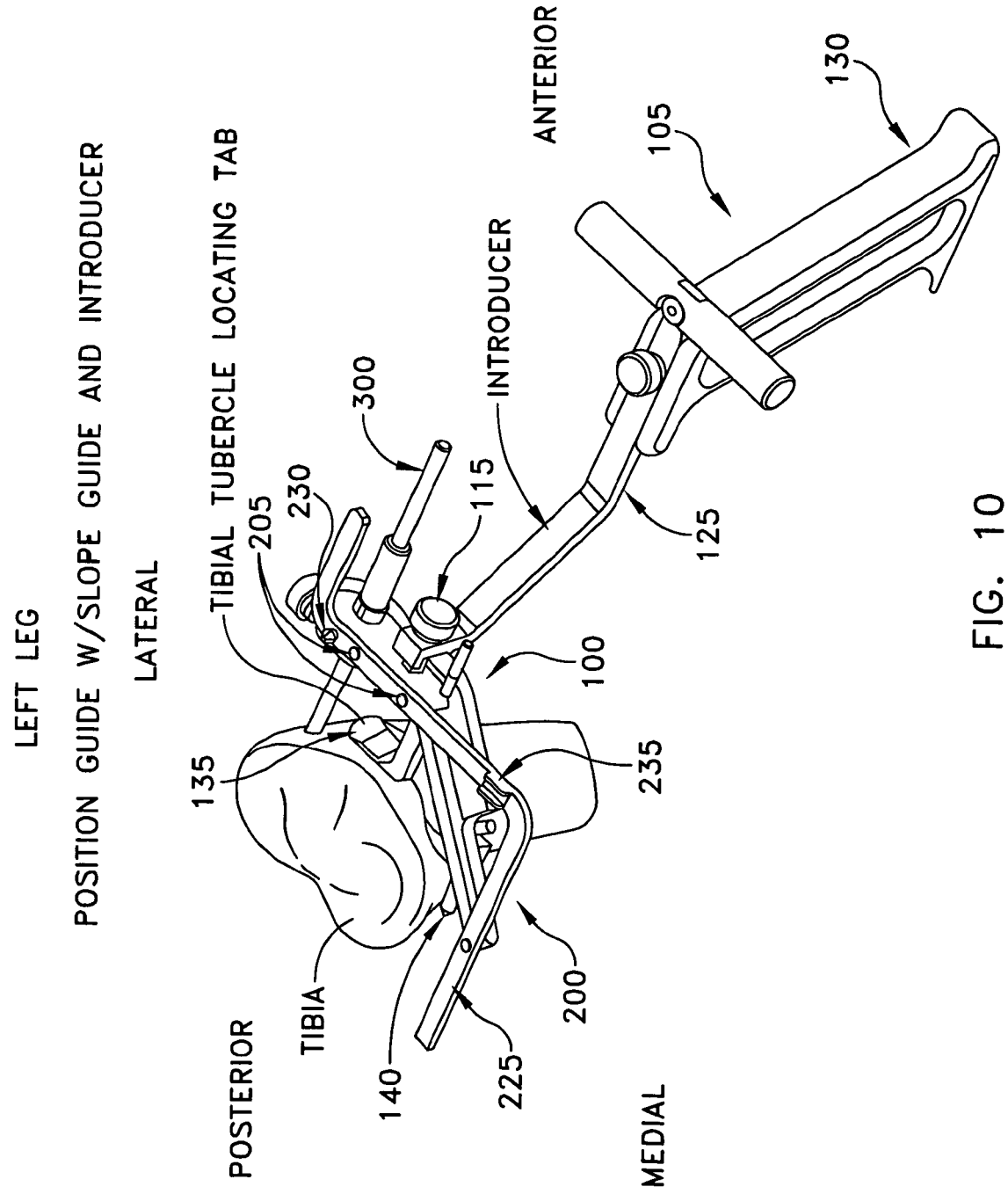
FIGS. 10-30 are schematic views showing a preferred method and apparatus for forming an appropriate osteotomy cut into the upper portion of the tibia, manipulating the tibia so as to open an appropriate wedge-like opening in the tibia, and then inserting an appropriate wedge-shaped implant into the wedge-like opening in the tibia.

3. Looking now at FIG. 10, an assembly comprising position guide 100 (FIGS. 10 and 16), slope guide 200 (FIGS. 10 and 11) and an introducer 105 (FIGS. 10 and 11) is advanced to the surgical site. Preferably the assembly of position guide 100, slope guide 200 and introducer 105 is pre-assembled prior to opening the skin. The assembly is assembled by mounting slope guide 200 to position guide 100 and then mounting introducer 105 to slope guide 200 and position guide 100 using a screw 115 (FIG. 10) passing through slope guide 200 and received in a threaded bore 120 formed in position guide 100.

In one preferred form of the invention, slope guide 200 may comprise two separate elements secured together, a base 210 and a guide element 215 connected by pins 205, with base 210 being formed out of a radio-translucent material (e.g., plastic) and with guide element 215 being formed out of a radio-opaque material (e.g., stainless steel), whereby guide element 215 will be visible under fluoroscopy and base 210 will be effectively invisible under fluoroscopy, as will hereinafter be discussed. In one preferred form of the invention, introducer 105 may comprise an arm 125 and a handle 130. Arm 125 and handle 130 may be formed as two separate elements secured together, or arm 125 and handle 130 may be formed as a singular construction.

4. Next, the foregoing assembly is maneuvered so that a tibial tubercle locating tab 135 (FIGS. 10 and 16) of position guide 100 is inserted between the patellar tendon (not shown) and the tibia, and so that tibial tubercle locating tab 135 is set against the tibial tubercle. In this way, the tibial tubercle provides a rough alignment guide for aligning position guide 100 with the tibia.

5. Using a lateral fluoroscope view, taken from the medial side at the level of the tibial plateau, the assembly is aligned so that the underside surface 220 of guide element 215 of slope guide 200 (FIG. 11) is aligned with the top of the medial condyle 75 of the tibia. See FIG. 11. Alternatively, if the surgeon prefers to shift the osteotomy slightly distally on the tibia, the top edge 225 of guide element 215 of slope guide 200 can be aligned with medial condyle 75, offsetting the osteotomy a fixed distance distally (e.g., 3 mm).

By forming the guide element 215 of slope guide 200 out of a radio-opaque material and by forming the base 210 of slope guide 200 out of a radio-translucent material, base 210 will be effectively invisible under fluoroscopy and guide element 215 will stand out in clear relief against the bone.

Figure 11:
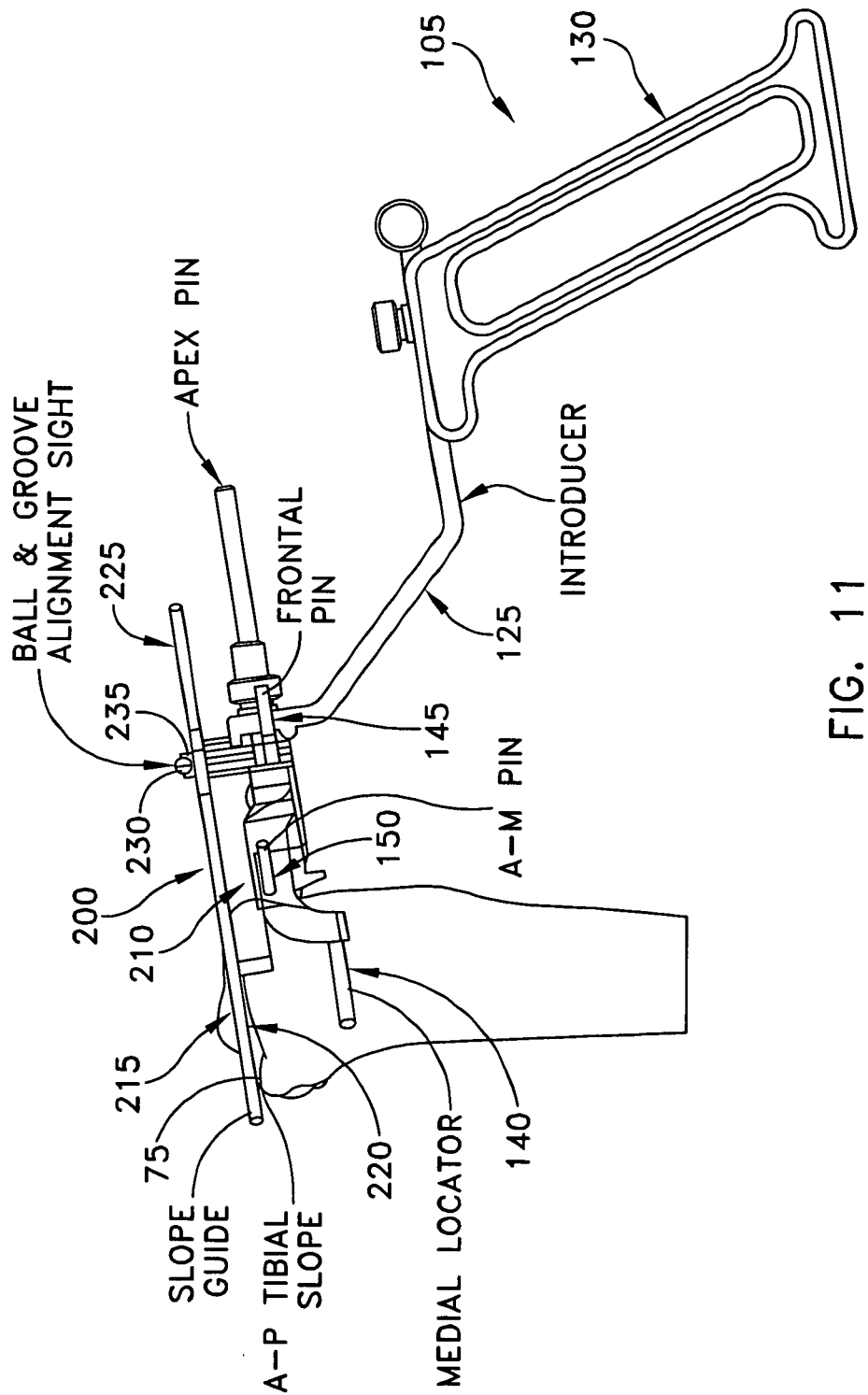
Figure 11A:
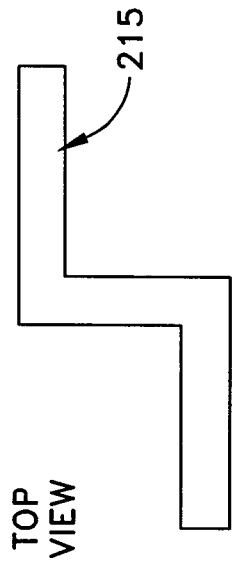
Figure 11B:
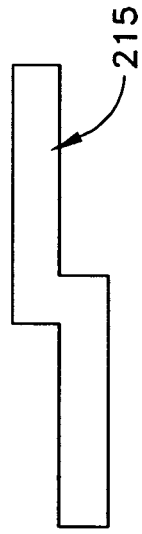
Figure 11C:
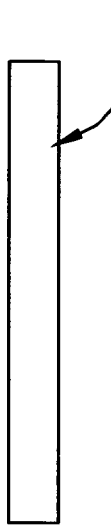

It should be noted that guide element 215 of slope guide 200 is preferably formed with a "Z shape" (FIGS. 10 and 11A) so as to provide additional functionality. More particularly, by forming guide element 215 with a "Z shape", several significant advantages are obtained. First, this construction permits guide element 215 to wrap around the perimeter of the tibia. Second, the "Z shape" of guide element 215 also operates to indicate if the slope guide is not vertically aligned with the level of the fluoroscope. More particularly, if slope guide 200 is not vertically aligned with the level of the fluoroscope, the "Z shape" of guide element 215 will appear as a jagged or zig-zag shape on the fluoroscope (FIG. 11B). However, if guide element 215 is vertically aligned with the level of the fluoroscope, then the guide element will appear as a straight line on the fluoroscope (FIGS. 11 and 11C). This vertical alignment is important, since it enables alignment of slope guide 200 (and hence position guide 100) with the medial condyle, i.e., the A-P slope plane.

Figure 16:
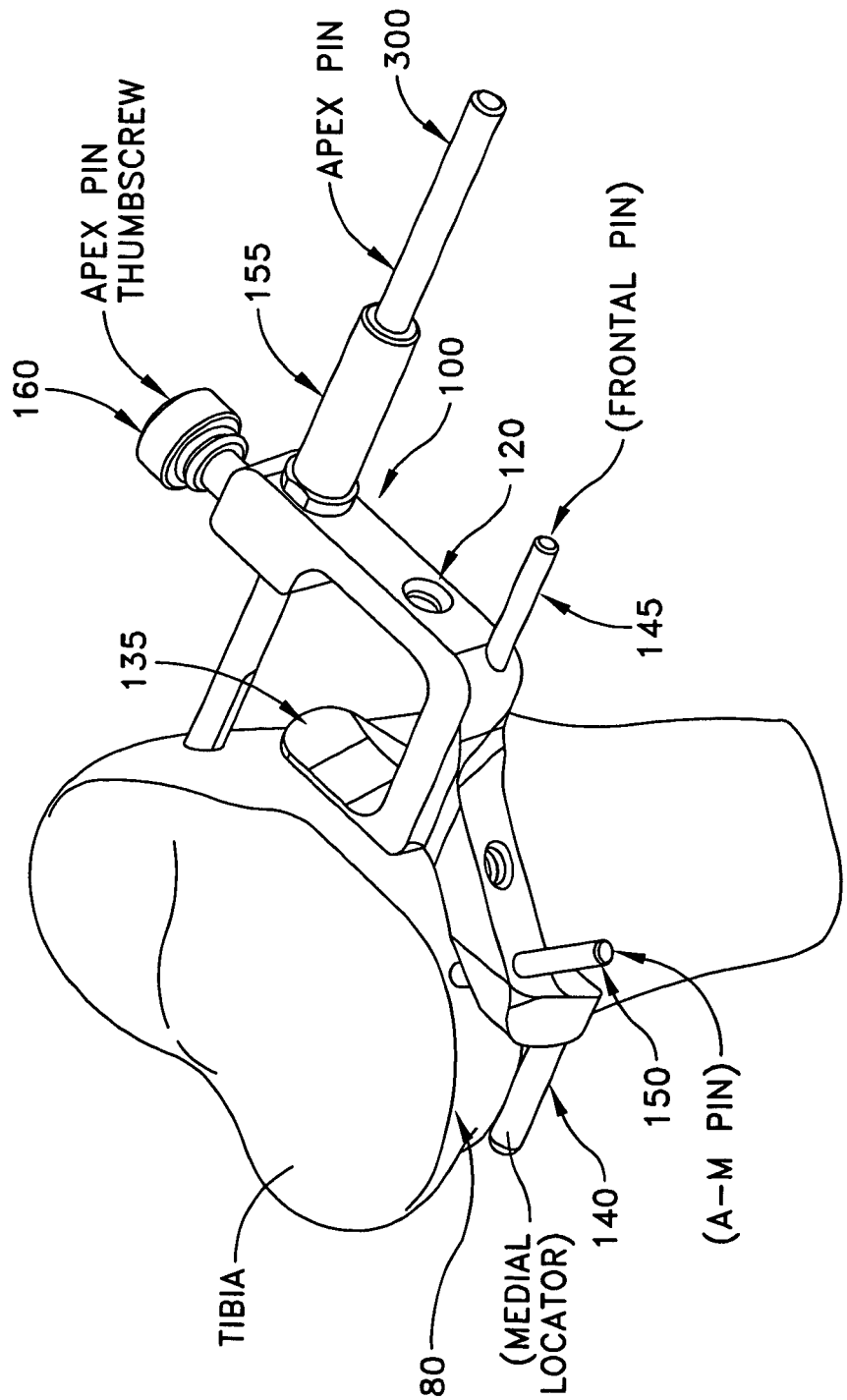

7. The assembly is then maneuvered so that the medial locating pin 140 (FIGS. 10, 11 and 16), preferably formed as a pin although it could also be formed as a tab, fin, etc., is located against the medial aspect 80 of the tibia (FIG. 16). As further adjustments in position are made, medial locating pin 140 is held in contact with the medial aspect of the tibia, thus ensuring proper alignment of the instrumentation. Medial locating pin 140 references the medial aspect of the tibia, thus setting the distance from the medial aspect of the tibia to the apex pin 300 (FIG. 10), as will hereinafter be discussed. This reference distance is used in conjunction with the sizing of the osteotomy implant 27 (FIG. 3) to ensure a proper tibial reconstruction, i.e., the distance from the medial aspect of the tibia to the center of apex pin 300 is designed to correspond to the distance from the medial aspect of the implant to the vertex of the wedge angle of the implant.

In another form of the invention, the reference distance may be the distance from the medial aspect of the tibia to a neutral axis of rotation in the bony hinge, which could be estimated by calculation. In this case, the distance from the medial aspect of the tibia to the neutral axis of the bony hinge would correspond to the distance from the medial aspect of the implant to the vertex of the wedge angle of the implant.

8. The assembly is then rotated around the primary tibial anatomical axis, by sliding introducer handle 130 in side-to-side motion, such that the instrumentation is aligned perpendicular to the frontal (coronal) plane, i.e., so that introducer 105 and apex pin 300 (see below) will extend parallel to the sagittal plane of the patient. To this end, slope guide 200 is provided with a ball 230 and a groove 235. With the fluoroscope arranged so that it is set in the lateral mode, with the image being taken from the medial side at the level of the tibial plateau (see FIG. 11), the assembly is maneuvered until ball 230 is centered in groove 235 (FIG. 11). When this occurs, the system is aligned with the sagittal plane (i.e., position guide 100 is disposed so that apex pin 300 will extend perpendicular to the frontal plane, as will hereinafter be discussed).

9. Thus, when slope guide 200 is aligned with the medial condyle 75, and when ball 230 is aligned with groove 235, the system is aligned with (i) the A-P slope, and (ii) the sagittal plane. In other words, when slope guide 200 is aligned with medial condyle 75, and when ball 230 is aligned with groove 235, the instrumentation is positioned so that apex pin 300 (see below) will be aligned with both the A-P slope and the sagittal plane, as will hereinafter be discussed.

10. With all of the previous adjustments in place, the positions of (i) tibial tubercle locating tab 135, (ii) slope guide 200, (iii) medial locating pin 140, and (iv) the ball and groove sights 230, 235 are verified. With all positions confirmed, the frontal pin 145 (FIG. 16) and the antero-medial (AM) pin 150 (FIG. 16) are inserted through position guide 100 and into the tibia. This secures position guide 100 to the tibia with the desired alignment.

Figure 14:
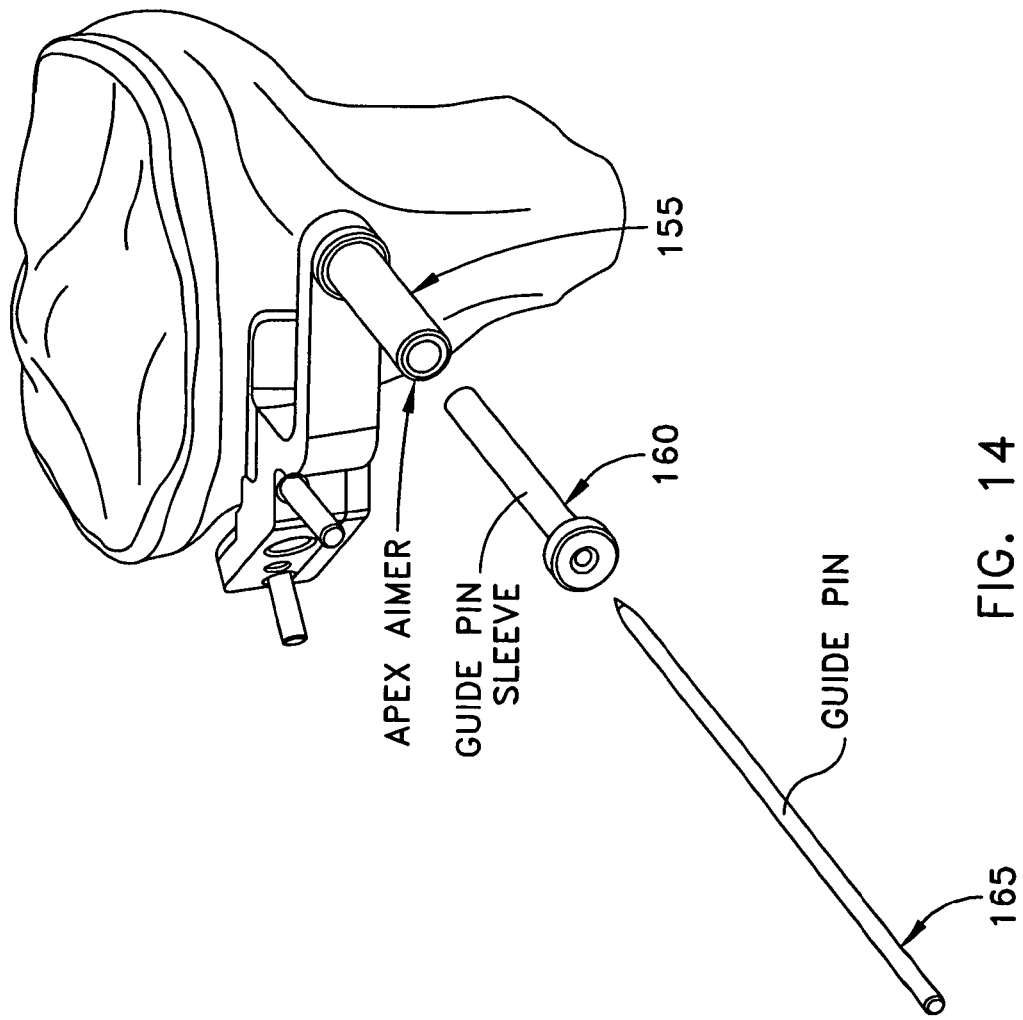

11. Next, apex pin 300 is inserted through position guide 100 and into the tibia. An apex aimer 155 (FIGS. 14 and 16) serves to guide apex pin 300 into the tibia with the proper orientation, i.e., so that apex pin 300 is positioned along the axis 70 formed at the lateral limit to the osteotomy cut, with apex pin 300 extending parallel to the A-P slope, perpendicular to the coronal plane, and within cutting plane 65. As a result, apex pin 300 can serve as the lateral stop for the osteotomy saw, whereby to clearly define the perimeter of the bony hinge, as will hereinafter be discussed. Apex pin 300 may be tapped or drilled into virgin bone, or it may be received in a pre-drilled hole (e.g., formed using apex aimer 155). A thumbscrew 160 (FIG. 16) may be used to secure apex pin 300 to position guide 100.

Apex pin 300 may be cylindrical in shape.

Figure 12:
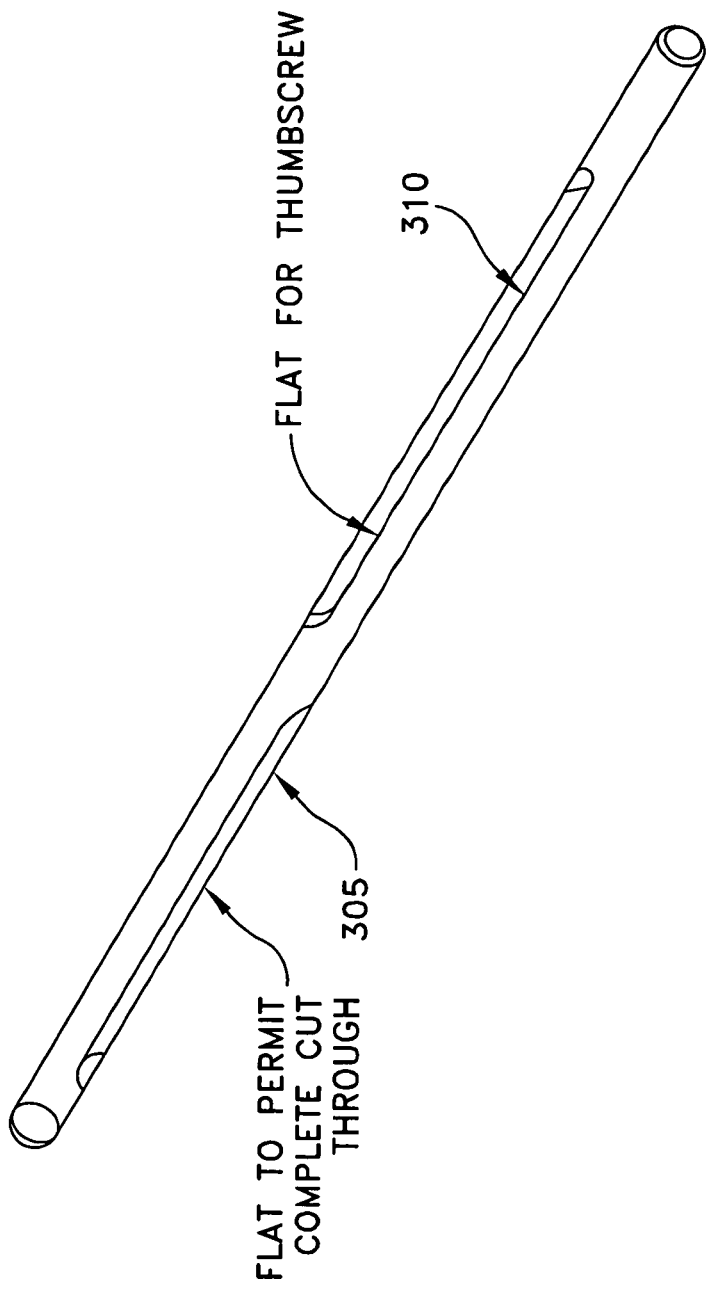
Figure 13:
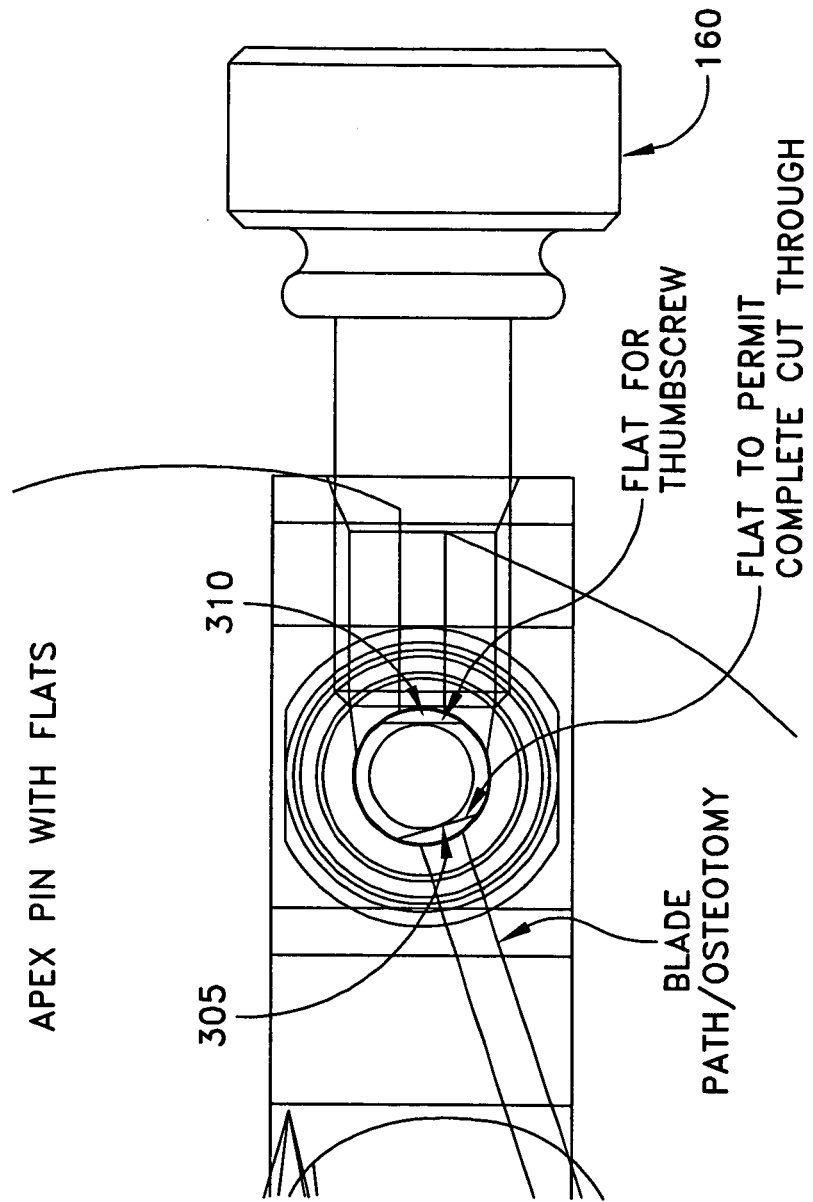

Alternatively, apex pin 300 may have a flat 305 (FIGS. 12 and 13) formed thereon to promote a complete cut-through of the osteotomy. Where apex pin 300 is provided with a distinct flat 305, it is preferably provided with a counterpart flat 310 (FIGS. 12 and 13), so that when apex pin 300 is in place and thumbscrew 160 is tightened against flat 310, the aforementioned flat 305 will be aligned with the osteotomy cut, whereby to ensure that the osteotomy blade cuts completely through the bone to reach the apex pin. See FIG. 13.

In another version of this construction (not shown), the flats 305, 310 may be diametrically opposed to one another, with thumbscrew 160 also being aligned with the osteotomy cut to make insertion of apex pin 300 less prone to error.

And in another embodiment of the present invention, apex pin 300 may be necked down to a smaller diameter in the area of the osteotomy. As a result of this construction, a slight relief area exists to accommodate the saw blade so as to help promote a complete cut-through, but does not require any specific orientation of the apex pin with respect to the osteotomy plane, as is the case where the apex pin is formed with distinct flats.

And in another version of the present invention, apex aimer 155 may be used with a guide sleeve 160 and a small-diameter guide pin 165 in order to first check the position of the small-diameter guide pin 165 relative to the desired axis for the apex pin, before thereafter deploying the larger-diameter apex pin 300. See FIG. 14. In this respect, it will be appreciated that repositioning a misdirected small-diameter guide pin 165 is easier and less traumatic to the host bone than repositioning a misdirected larger-diameter apex pin 300.

Figure 15:
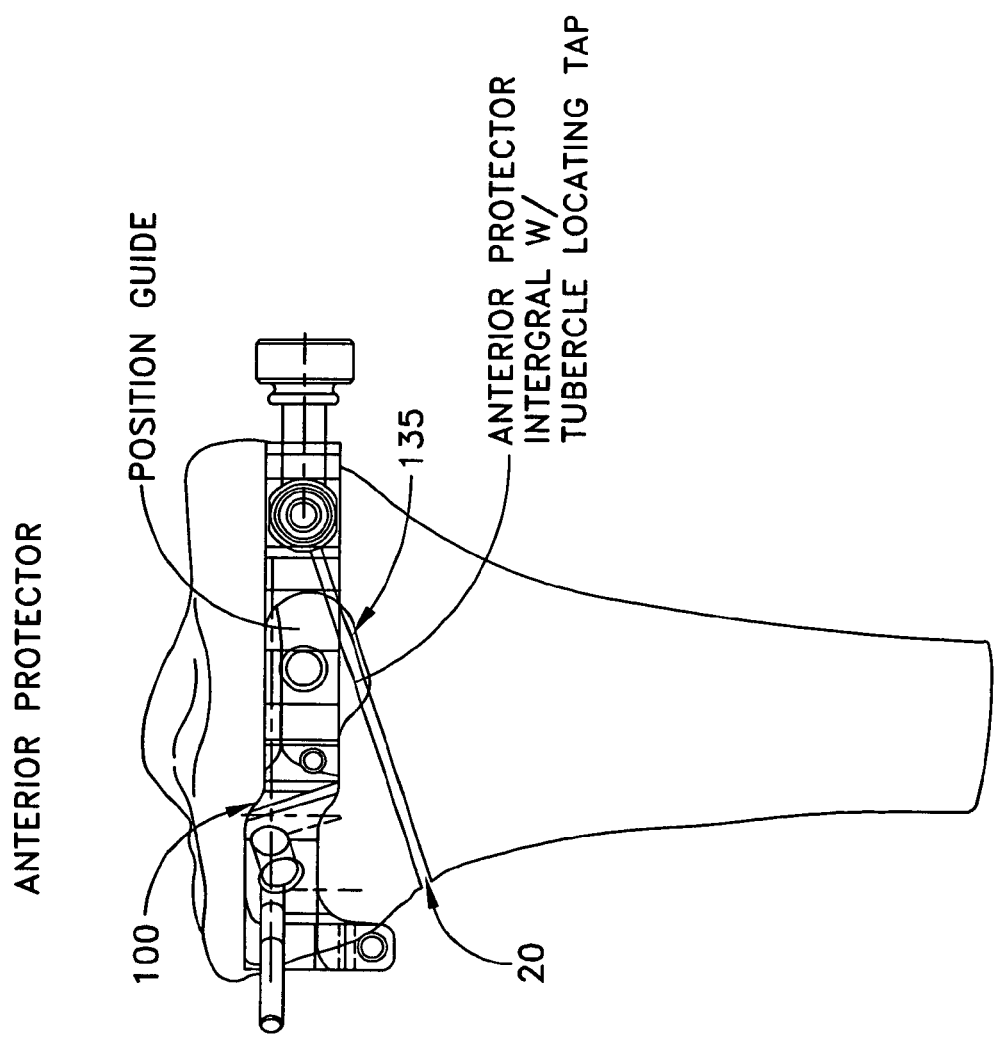

As seen in FIG. 15, tibial tubercle locating tab 135 is preferably sized so that it also functions as an anterior protector, by providing a protective shield between the oscillating saw blade (to be used later in the procedure to form the osteotomy cut 20) and the anterior soft tissue structures, e.g., the patellar tendon.

12. By virtue of the foregoing, it will be seen that apex pin 300 is deployed in the patient's tibia so that the apex pin extends (i) parallel to the A-P slope of the tibia, and (ii) parallel to the sagittal plane of the patient. As a result, when the osteotomy cut is subsequently formed in the bone (see below) by cutting along the osteotomy cut plane until the apex pin is engaged, so that the perimeter of the bony hinge is defined by the location of the apex pin, the bony hinge will extend (i) parallel to the A-P slope of the tibia, and (ii) parallel to the sagittal plane of the patient. By ensuring that apex pin 300 is set in this fashion, and hence ensuring that the bony hinge is so created, the final configuration of the tibia can be properly regulated when the bone cut is thereafter opened so as to form the open wedge osteotomy.

Figure 17:
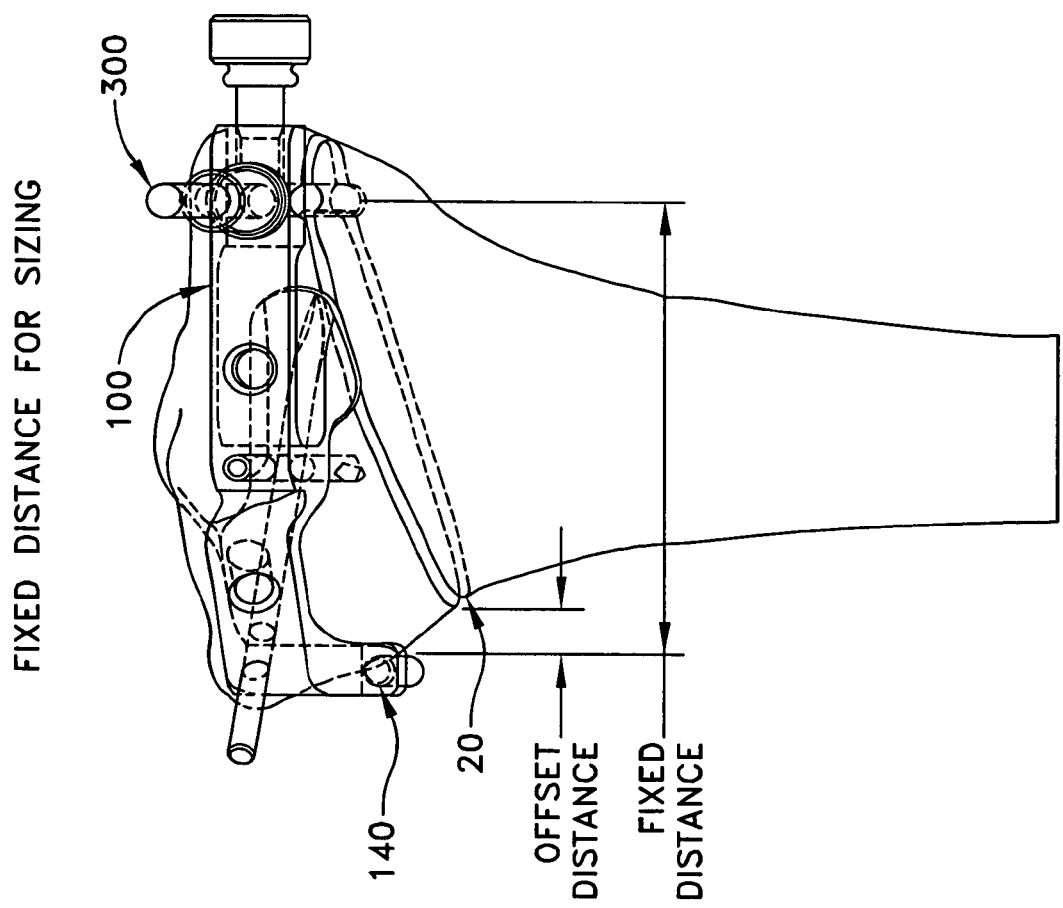

13. Once apex pin 300 has been properly positioned in the bone, slope guide 200 and introducer 105 are removed, leaving position guide 100 properly aligned on, and secured to, the tibia, and apex pin 300 properly deployed into the tibia (i.e., with apex pin 300 extending parallel to the A-P slope and parallel to the sagittal plane of the patient). See FIG. 16. The size of position guide 100 and the associated instrumentation is used to prepare the osteotomy to fit the particular implant sizing of small, medium or large. More particularly, the medial locating pin 140, the size of position guide 100, and apex pin 300 all combine to implement the implant sizing scheme. As seen in FIG. 17, medial locating pin 140, position guide 100 and apex pin 300 combine to provide a known, fixed distance from the medial aspect of the tibia to the apex pin. The size of the planned osteotomy is then set, allowing a specifically-sized implant (e.g., small, medium or large) to nominally fit between the medial aspect and the apex pin.

In the embodiment shown in FIG. 17, there is a known lateral offset between medial locating pin 140 and the entry point of the osteotomy. The implant size is reduced slightly to factor in this offset distance so as to yield a proper fit.

In an alternative construction, medial locating pin 140 may be perfectly aligned with the entry point of the planned osteotomy (not shown).

14. Looking next at FIG. 18, keyhole drill guide 400 is then attached to position guide 100 by passing keyhole drill guide 400 over frontal pin 145 and apex aimer 155. Keyhole drill guide 400 is then secured in this position with thumbscrew 405. At this point, a distal pin 410 is inserted through keyhole drill guide 400 and into the tibia. Distal pin 410 further secures the instrumentation to the tibia. Next, a surface locator pin 415 is inserted through keyhole drill guide 400. Surface locator pin 415 slides through keyhole drill guide 400 until the distal tip of surface locator pin 415 contacts the surface of the tibia. For the purposes of the present invention, this surface may be referred to as the "antero-medial surface" or the "A-M surface", which is the anatomical surface of the tibia corresponding to the antero-medial approach of the osteotomy. When surface locator pin 415 contacts the A-M surface, the surface locator pin can act as an indicator as to the location of the A-M surface. This information can then be used to set the depth of the keyholes to be formed in the tibia (see below) for an improved implant fit.

Figure 29:
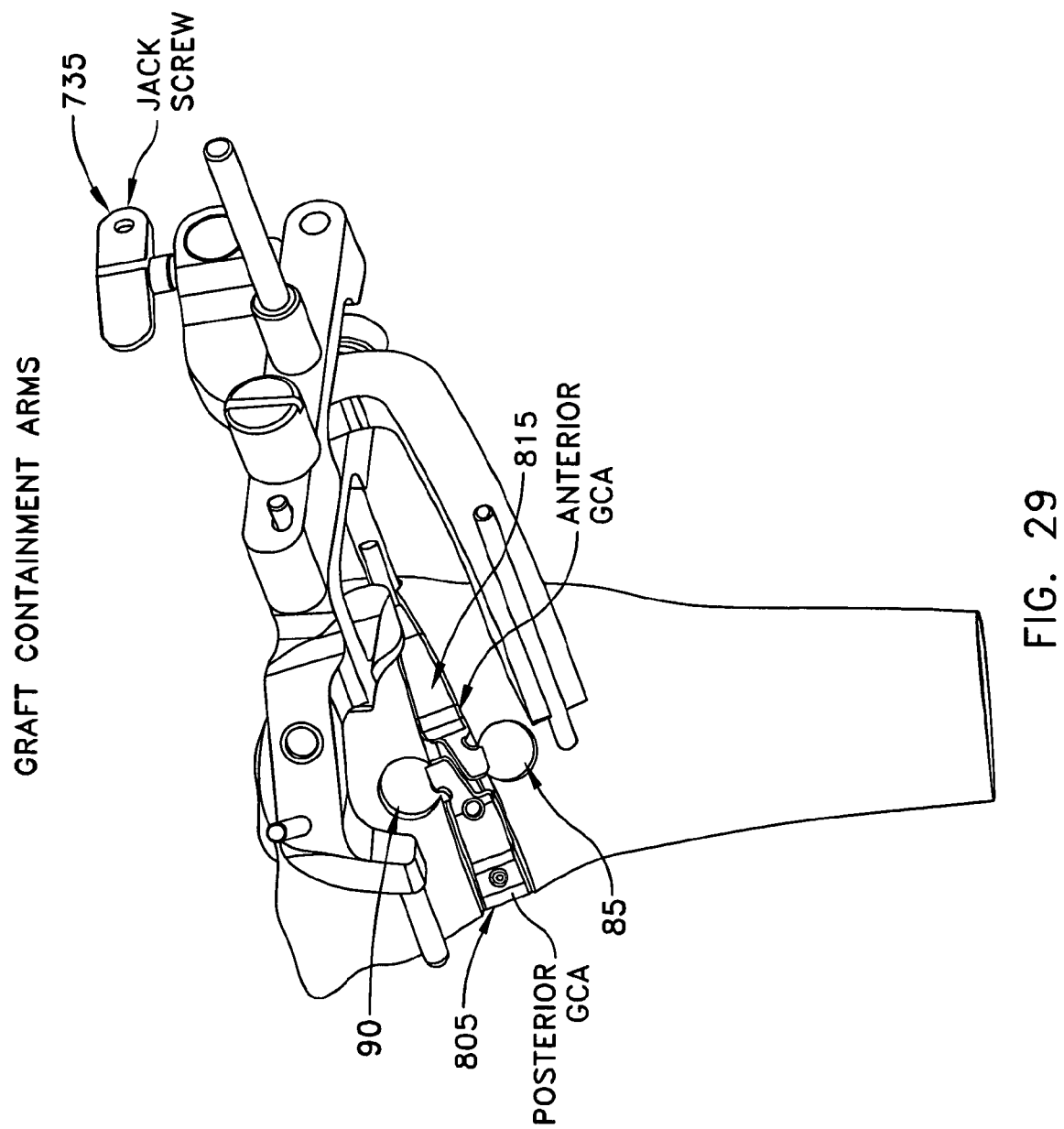

Next, an end mill 420 is inserted into the distal hole 425 (i.e., the bottom hole 425) of keyhole drill guide 400 and drilled until a stop flange 430 on end mill 420 contacts the proximal end of surface locator pin 415, whereby to form the distal keyhole 85 (FIG. 21) in the tibia. The drilling procedure is then repeated for the proximal hole 435 (i.e., the top hole 435), whereby to form the proximal keyhole 90 (FIG. 21) in the tibia. While it is possible to drill the proximal keyhole before the distal keyhole, it is generally preferable to drill the distal keyhole first. This is because drilling the distal keyhole before the proximal keyhole reduces the possibility that the sloping nature of the bone will cause a later-drilled keyhole to slip into an earlier-drilled keyhole. It should be appreciated that keyhole drill guide 400 is configured so that distal hole 425 and proximal hole 435 will overlap the osteotomy cutting plane 65 to some extent (FIG. 21), so that when osteotomy cut 20 is thereafter formed and the tibia subsequently opened so as to create the wedge-like opening 25, distal keyhole 85 and proximal keyhole 90 will overlap, and communicate with, the wedge-like opening 25 (FIG. 29).

15. Once the two implant keyholes have been drilled into the tibia, end mill 420 is removed, thumbscrew 405 is loosened, and then keyhole drill guide 400 is removed.

Figure 19:
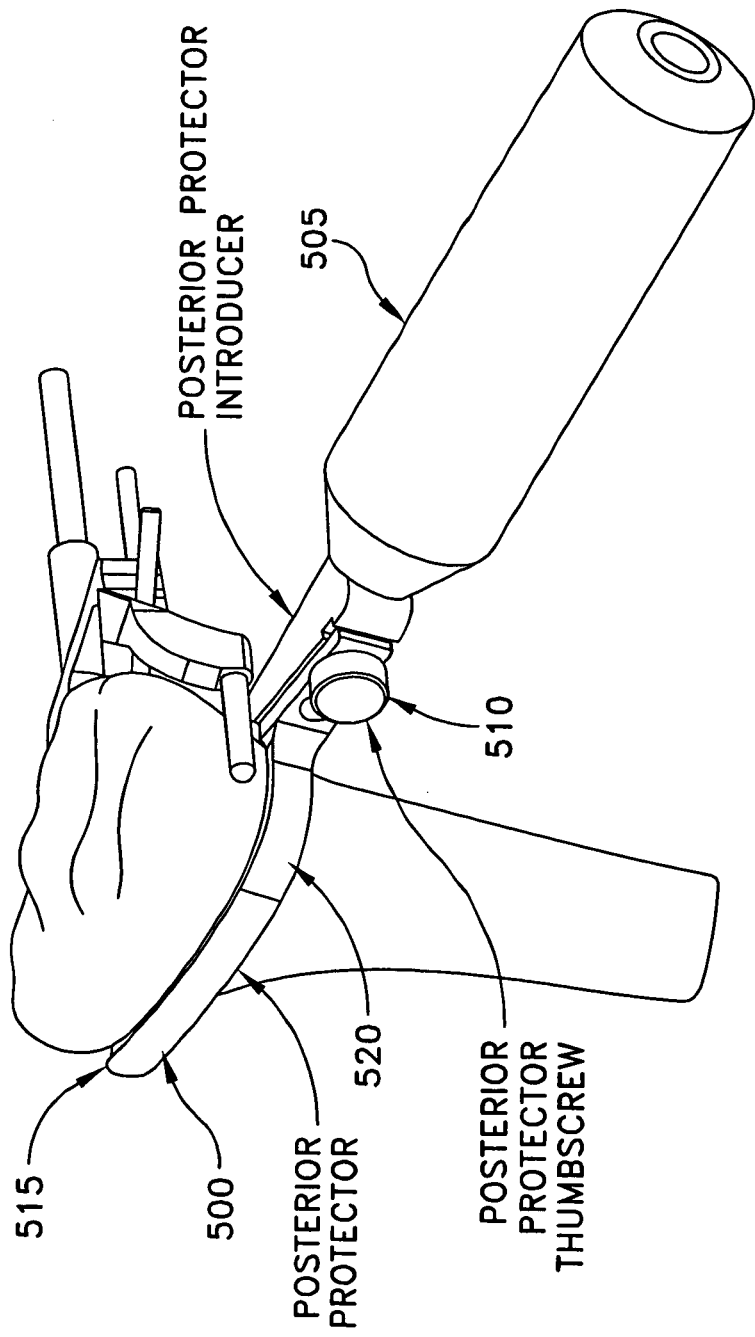
Figure 21:
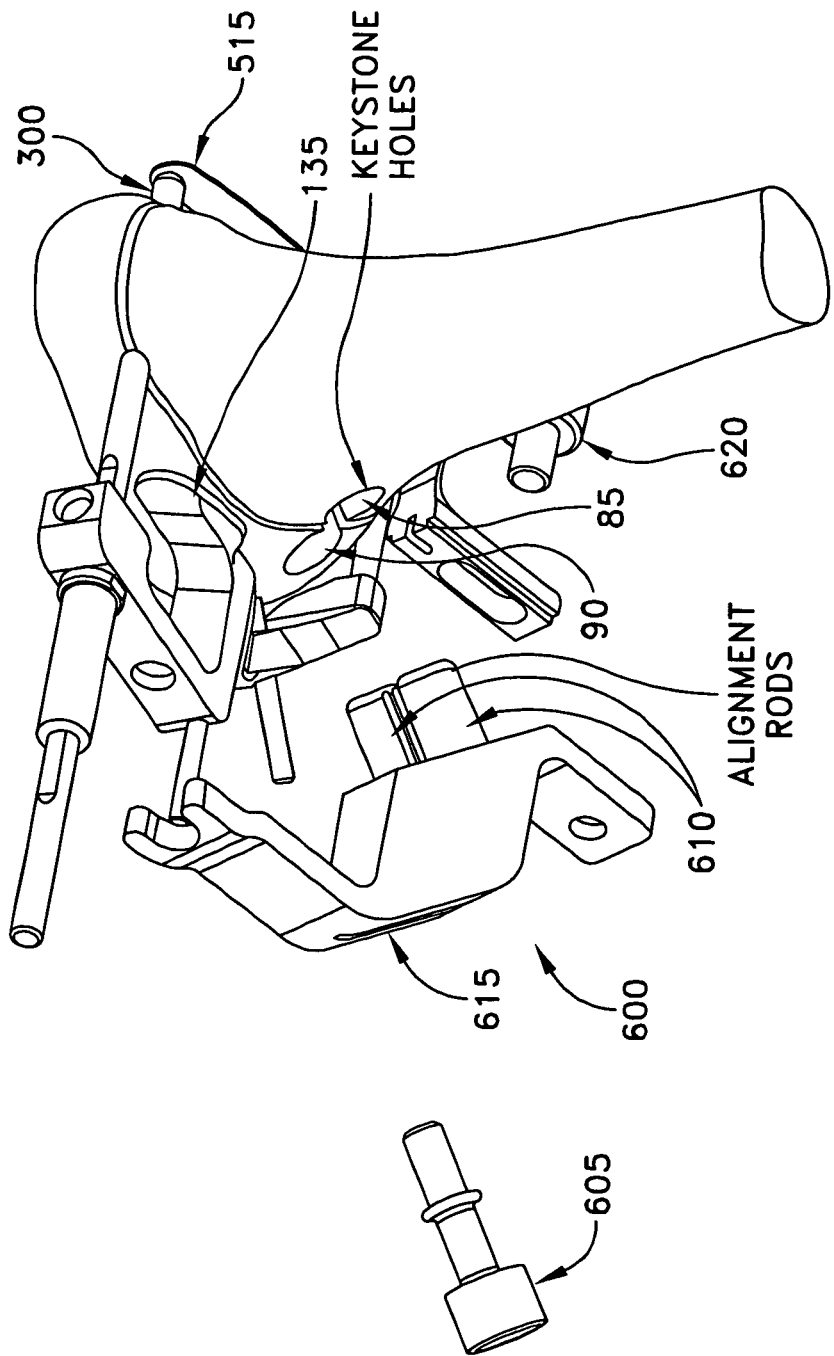

16. Next, and looking now at FIG. 19, posterior protector 500 is attached to an introducer 505 with a thumbscrew 510. The far tip 515 (FIGS. 19 and 21) of posterior protector 500 is inserted into the incision. Posterior protector 500 is preferably formed out of a somewhat flexible material so as to allow the posterior protector to flex slightly to allow easier insertion into the incision and to conform to the shape of the posterior cortex. See FIG. 19. Posterior protector 500 is inserted by gradually sliding it around the posterior cortex of the tibia until far tip 515 of posterior protector 500 substantially crosses the axis of, and in some cases actually engages, apex pin 300 (FIG. 21). Posterior protector 500 preferably comprises a stiff curved portion 520 proximal to flexible tip 515. Once posterior protector 500 has been properly deployed, the thumbscrew 510 is unscrewed, and introducer handle 505 is removed.

17. Looking next at FIG. 20, cutting guide 600 is then attached to position guide 100 and secured in place using cutting guide thumbscrew 605. Cutting guide 600 comprises alignment rods 610 that extend from the cutting guide into the pre-drilled keyholes 85, 90 (FIG. 21) to assist with cutting alignment. More particularly, alignment rods 610 ensure proper alignment between cutting guide 600, its cutting slot 615 (FIGS. 20 and 21) and the pre-drilled keyholes 85, 90 previously formed in the tibia with end mill 420 and, ultimately, ensure the desired fit between the implant and the tibia.

Figure 20:
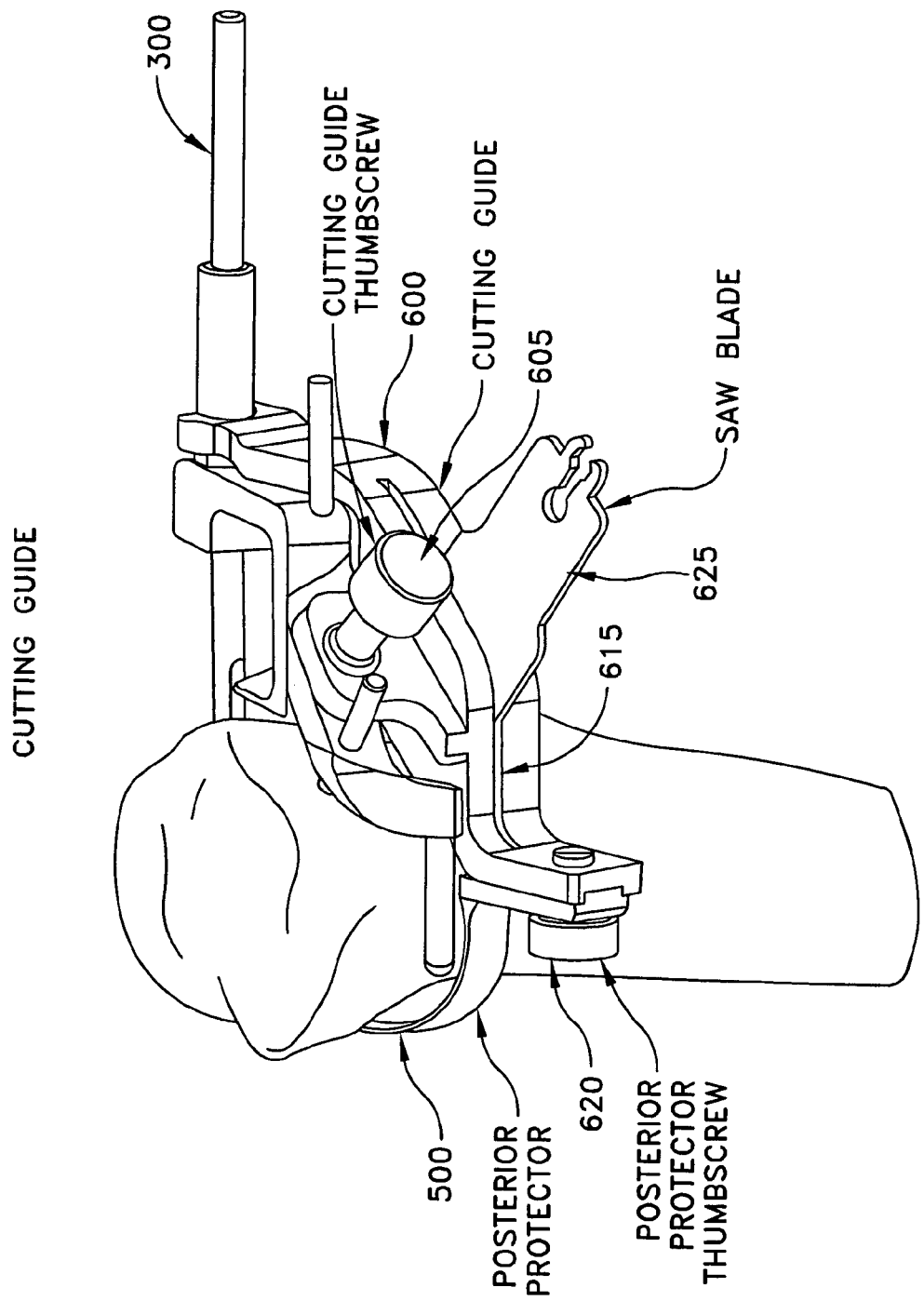

Then, posterior protector 500 is attached to cutting guide 600 using thumbscrew 620 (FIG. 20).

At this point, the instrumentation is ready to form the osteotomy cut, with cutting slot 615 of cutting guide 600 properly aligned with the osteotomy cut plane, apex pin 300 properly positioned at the far (lateral) limit of the osteotomy cut, tibial tubercle locating tab 135 forming a protective shield for the patellar tendon, and with posterior protector 500 forming a protective shield for the vascular and neurological structures at the back of the knee. In this respect it should be appreciated that cutting guide 600 is sized and shaped, and cutting slot 615 is positioned, so that, in addition to being aligned with the apex pin 300, the entry point of the cutting plane into the tibia is located at an appropriate location on the tibia's medial neck 66.

18. Next, a saw blade 625 (attached to an oscillating saw, not shown) is inserted into cutting slot 615 of cutting guide 600. The osteotomy cut is then made by plunging the oscillating saw blade through cutting slot 615 and into the bone (FIG. 20). The saw blade will cut completely through the medial and posterior cortices. The saw is operated until saw blade 625 contacts posterior protector 500 and apex pin 300. As the saw blade cuts through the tibia, it is constrained by cutting slot 615, apex pin 300 and posterior protector 500, so that the saw blade may only cut bone along the osteotomy plane, up to but not beyond the desired location of the bony hinge, and does not cut soft tissue. During cutting, tibial tubercle locating tab 135 also ensures that the saw blade will not inadvertently cut the patellar tendon.

After saw blade 625 forms the desired osteotomy cut 20 along the cutting plane, the saw blade is removed, and a hand osteotome (not shown) of the sort well know in the art is inserted through cutting slot 615 and into the osteotomy cut 20, and then the cut is completed through the posterior cortical bone near apex pin 300 and posterior protector 500. Then the hand osteotome is removed.

At this point the osteotomy cut 20 has been completed, with the osteotomy cut terminating on the lateral side at apex pin 300, so that the bony hinge is properly positioned at the desired location, i.e., parallel to the A-P slope and perpendicular to the coronal plane.

Next, thumbscrew 620 is loosened and posterior protector 500 removed. Then thumbscrew 605 is loosened and cutting guide 600 is removed.

At this point, the desired osteotomy cut 20 has been formed in the tibia, with keyholes 85 and 90 formed below and above, respectively, the osteotomy cut.

In order to complete the procedure, the bone must now be opened so as to reconfigure the tibia to the desired geometry, and then the tibia stabilized with the desired configuration, e.g., by inserting a wedge-shaped implant 27 into wedge-like opening 25.

19. Looking next at FIG. 22, opening jack 700 is assembled onto the instrumentation by receiving frontal pin 145 in a hole 705 formed in jack arm 710, by receiving apex aimer 155 in another hole 715 formed in jack arm 710 and jack arm 725, and by receiving distal pin 410 in a slot 720 formed in jack arm 725. Opening jack 700 is secured to position guide 100 with a thumbscrew 730.

Figure 23:
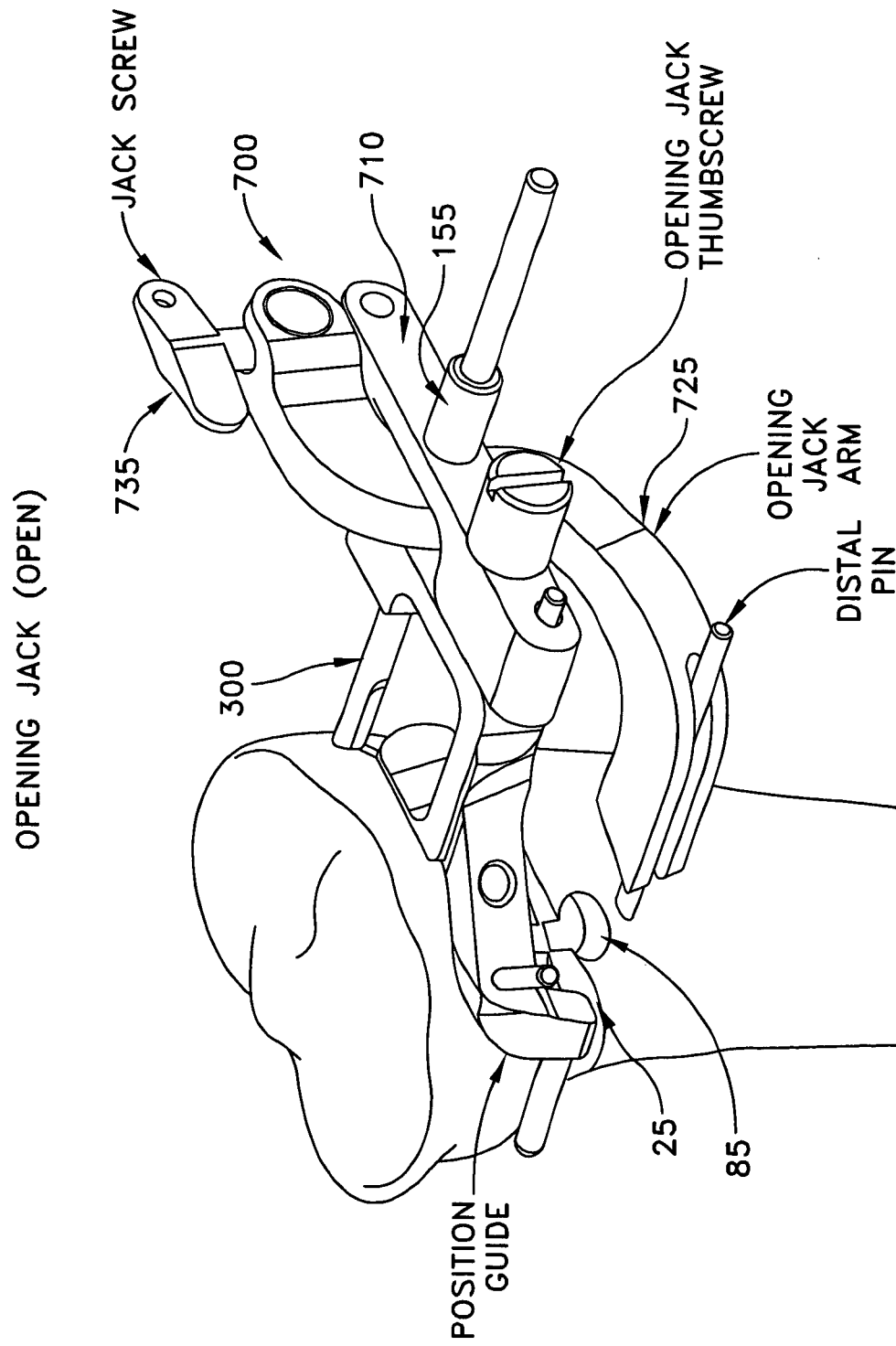
Figure 23A:
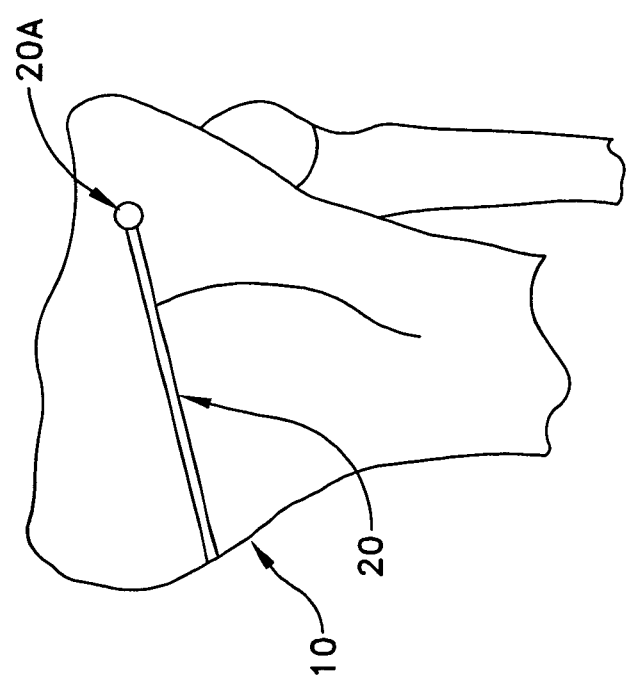

Once opening jack 700 is in place, the jack is opened by rotating jack screw 735. This causes jack arm 725 to pivot about apex aimer 155 so as to open the jack and thereby open the desired wedge-like opening 25 in the tibia. See FIG. 23. Preferably the patient's lower leg is manipulated as jack screw 735 is turned so as to assist opening of the bone. As the wedge-like opening 25 is created in the bone, the tibia will be reoriented in a highly controlled manner, due to the fact that the bony hinge will be precisely positioned at axis 70 through the use of apex pin 300, i.e., the bony hinge will extend parallel to the A-P slope and parallel to the sagittal plane. Furthermore, as the wedge-like opening 25 is created in the bone, the risk of bone cracking will be minimized, due to the fact that apex pin 300 forms an oversized hole 95 (FIGS. 23A and 27) at the lateral end of the bone cut, i.e., "oversized" relative to the thickness of the osteotomy cut, whereby to reduce the occurrence of stress risers and the like.

20. Then, with opening jack 700 still in place, an implant is positioned in the wedge-like opening 25. If desired, the implant may be a "generic" implant such as the implant 27 shown in FIG. 3. More preferably, however, and looking now at FIG. 24, there is shown a wedge-shaped implant 800 formed in accordance with the present invention. Wedge-shaped implant 800 is characterized by a wedge-like side profile configured to match the geometry of the wedge-like opening 25. Preferably, wedge-shaped implant 800 is also formed so as to have a U-shaped top profile, such that it can form a barrier about the perimeter of the wedge-like opening 25, whereby to constrain graft material (e.g., bone paste, bone cement, etc.) which may be positioned within the interior of the wedge-like opening 25. In one preferred form of the present invention, wedge-shaped implant 800 is formed so as to have an asymmetric configuration when viewed in a top view, so as to mate with the geometry of the tibia when the implant is positioned using an antero-medial approach. Wedge-shaped implant 800 may be formed out of absorbable material or non-absorbable material, as desired.

Figure 25:
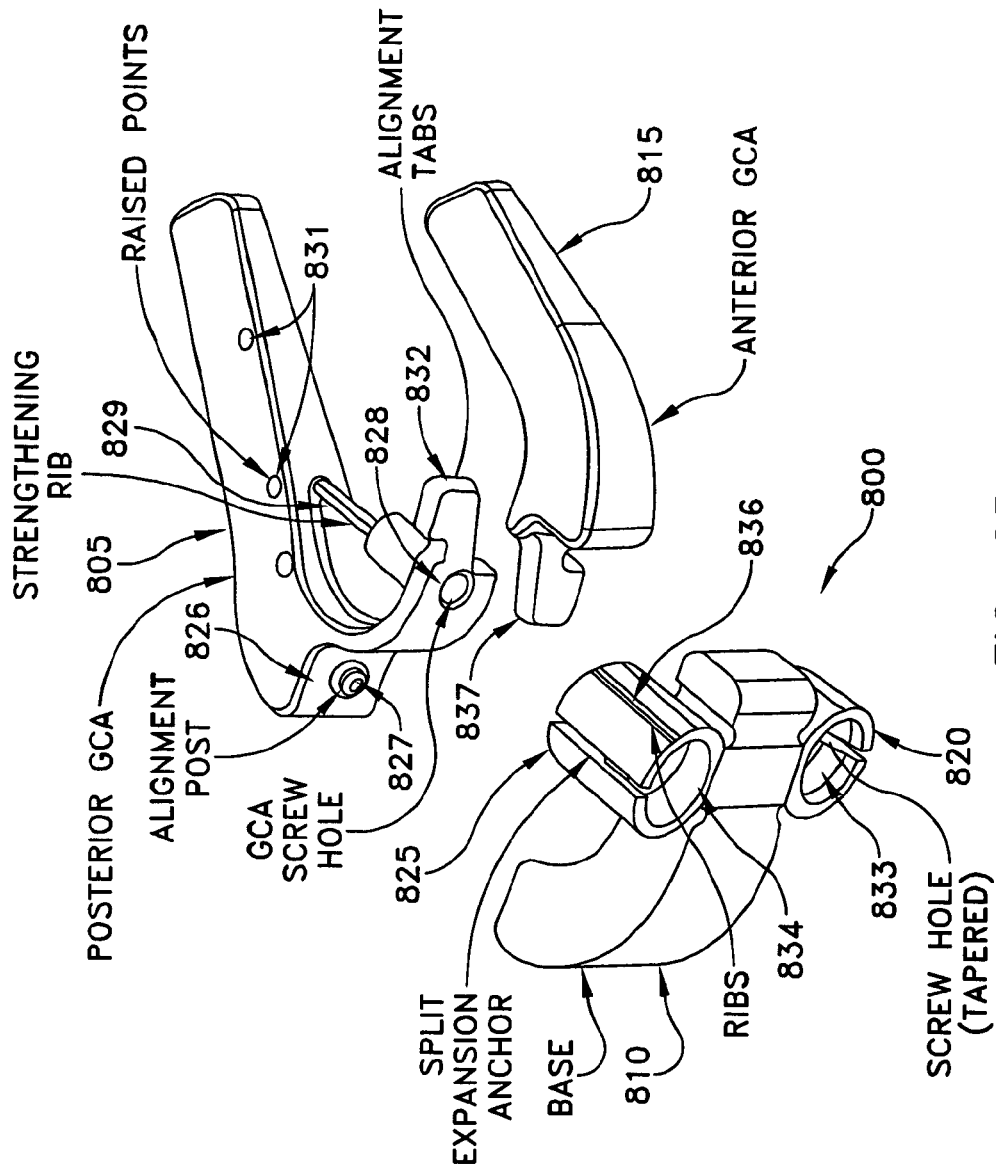
Figure 26:
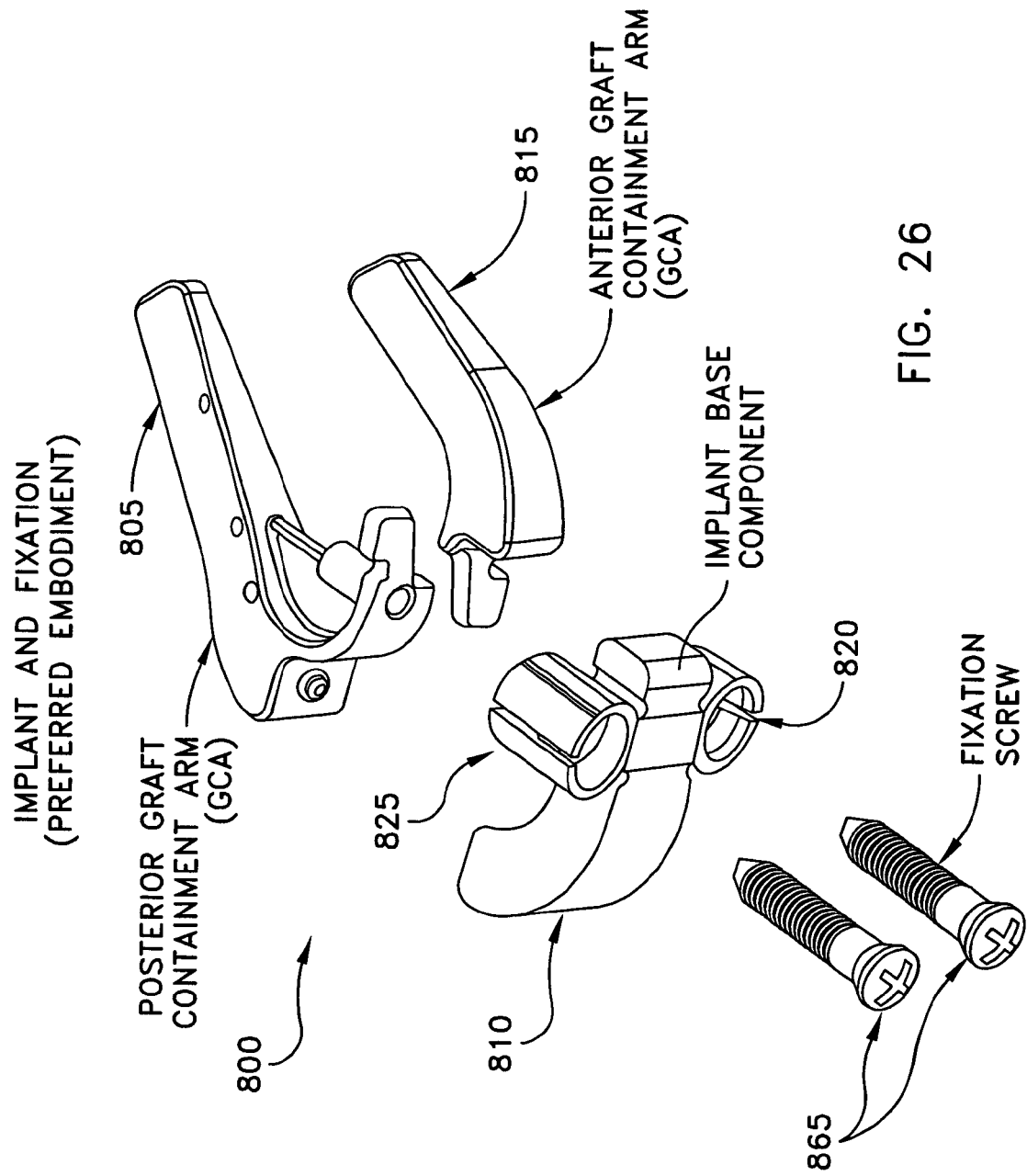

In one preferred form of the invention, and looking now at FIGS. 25 and 26, implant 800 preferably comprises a three-part assembly, comprising posterior graft containment arm (GCA) 805, a base 810 and an anterior graft containment arm (GCA) 815. The individual components of implant 800 may each be formed out of absorbable material and/or non-absorbable material, as desired. Furthermore, where one or more of the implant components is formed out of an absorbable material, the absorption characteristics of the material may vary as desired. By way of example but not limitation, base 810 may be formed out of a relatively slowly-absorbing material, while posterior graft containment arm (GCA) 805 and anterior graft containment arm (GCA) 815 may be formed out of a relatively faster-absorbing material. Base 810 preferably comprises a pair of keys 820, 825.

In one preferred form of the invention, implant 800 is formed so that posterior graft containment arm (GCA) 805 has a generally wedge-shaped profile including an engagement seat 826 comprising an alignment post 827, and an introducer hole 828 opening on the antero-medial side of the component for engagement with introducer 845 (see below). A strengthening rib 829 is preferably provided as shown. Additionally, raised points or dimples 831 may be provided to help fix GCA 805 to the bone. An alignment tab 832 is provided for extension into upper keyhole 90 (FIG. 29) when GCA 805 is positioned in the wedge-shaped opening 25.

And in one preferred form of the invention, base 805 is formed so that its keys 820, 825 each includes a tapered axial bore 833, 834, respectively, with the keys being slotted longitudinally so as to permit expansion of the keys when screws 865 are thereafter deployed in the tapered axial bores. External ribs 836 may be provided on the outer surfaces of keys 820, 825 so as to help fix keys 820, 825 in keyholes 85, 90, respectively, as will hereafter be discussed in further detail. An alignment mechanism (not shown) is provided for mating with alignment post 827 of GCA 805.

Anterior graft containment arm (GCA) 815 also comprises a generally wedge-shaped profile, and an alignment tab 834 is provided for extension into lower keyhole 85 when GCA 815 is positioned in the wedge-shaped opening 25.

Horseshoe implant 800 is preferably assembled in situ.

More particularly, a pre-assembled assembly comprising posterior graft containment arm (GCA) 805, an implant trial base 830 and two guide sleeves 835, 840 are first inserted into wedge-like opening 25 in the bone using an introducer 845. See FIGS. 27 and 28.

Figure 27:
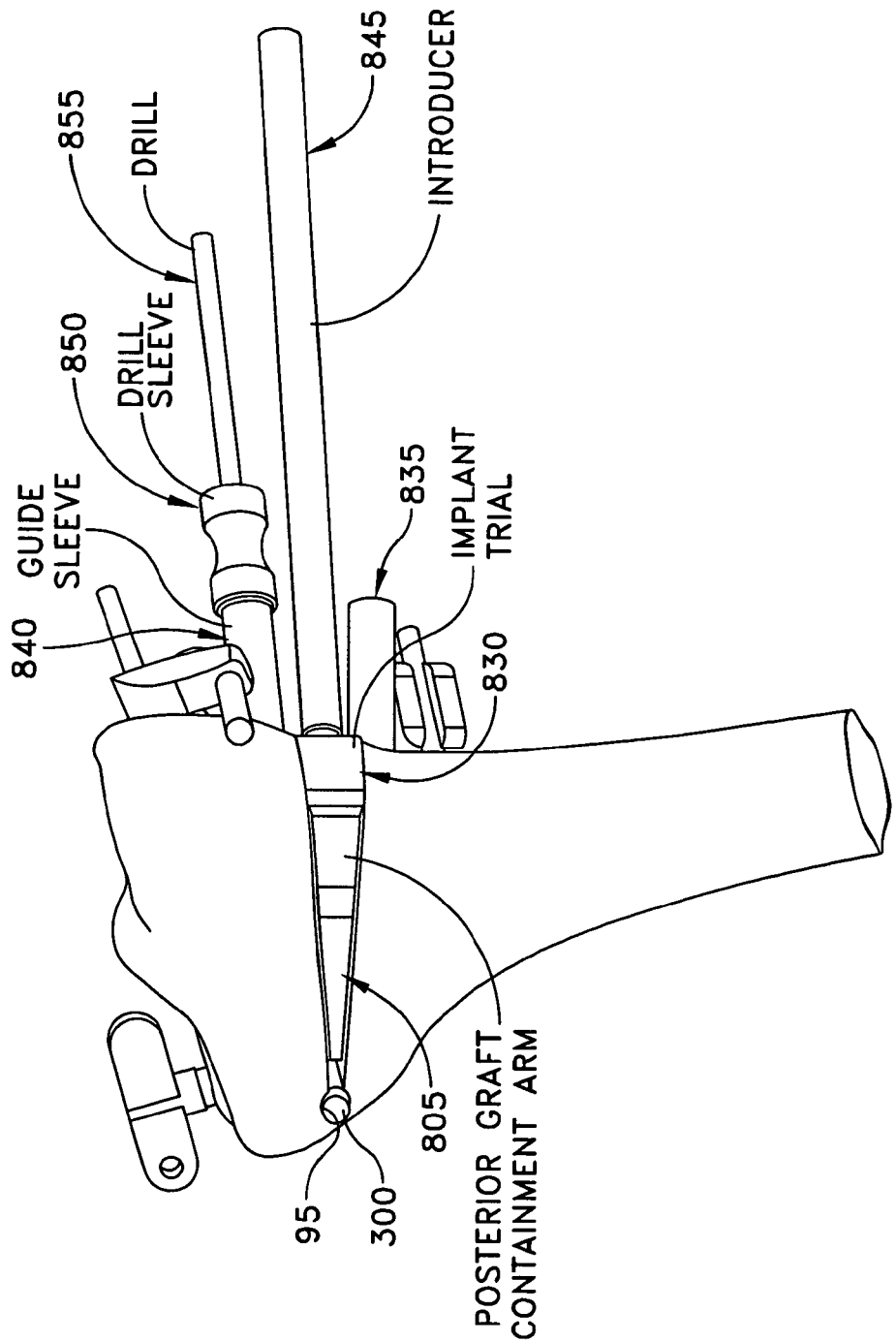
Figure 28:
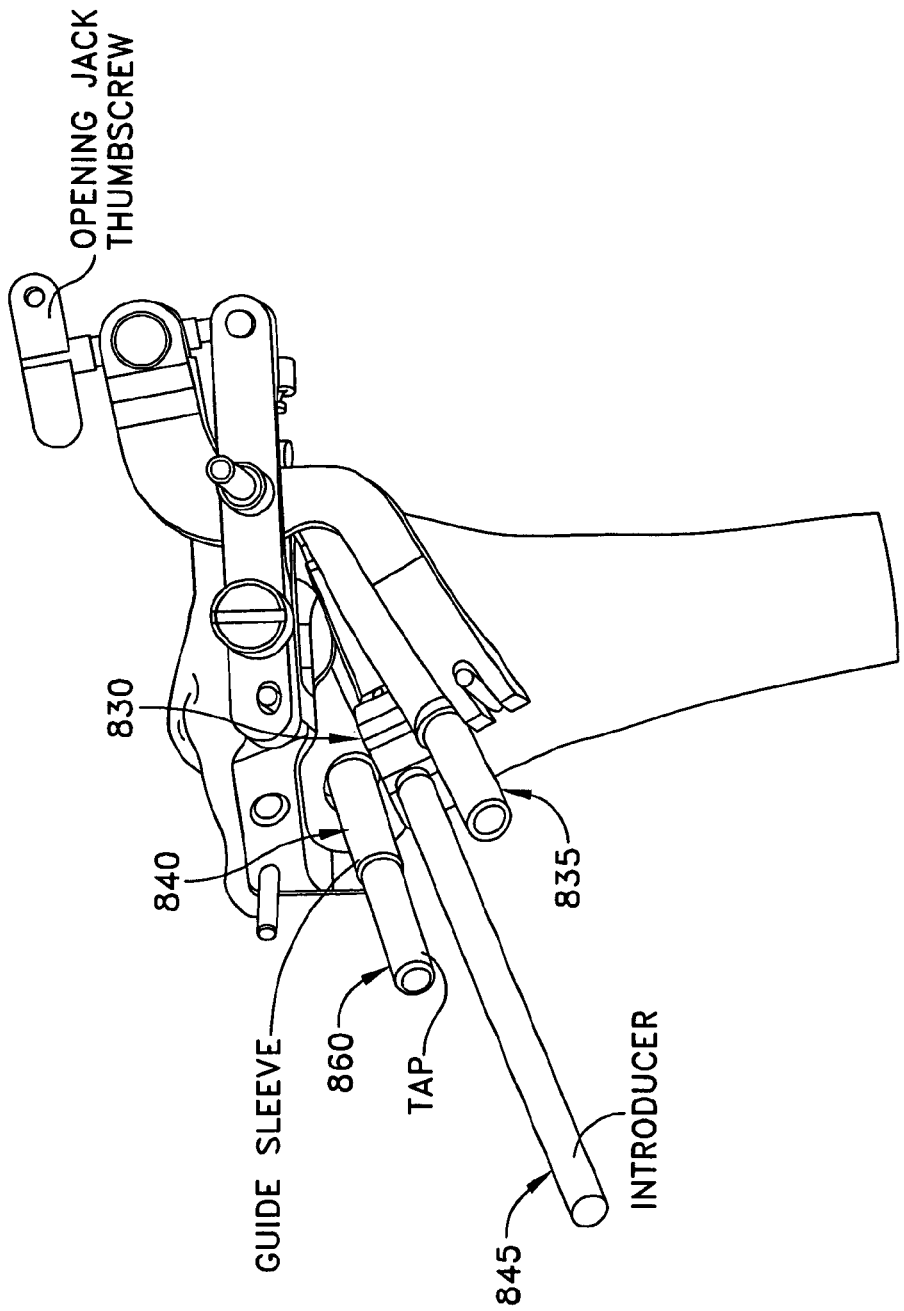

Next, a drill sleeve 850 and a drill 855 are inserted into guide sleeve 840 (FIG. 27). An upper hole is drilled into the tibia with the drill. The drilling procedure is then repeated for guide sleeve 835 so as to create a lower hole. Then drill sleeve 850 and drill 855 are removed from the surgical site. Next, a tap 860 is inserted into guide sleeve 840 and the upper hole is tapped. See FIG. 28. Then the tap is inserted into guide sleeve 835 and the lower hole is tapped. Then tap 860 is removed from the surgical site.

21. Next, posterior graft containment arm (GCA) 805 is released from introducer 845, and then introducer 845 and implant trial base 830 are removed.

22. Then, if desired, graft material is packed into the osteotomy opening.

23. Next, anterior graft containment arm (GCA) 815 is placed into the osteotomy opening and aligned with the prepared implant holes. See FIG. 29. If necessary, jack screw 735 is rotated as needed so as to facilitate insertion of anterior GCA 815.

Figure 30:
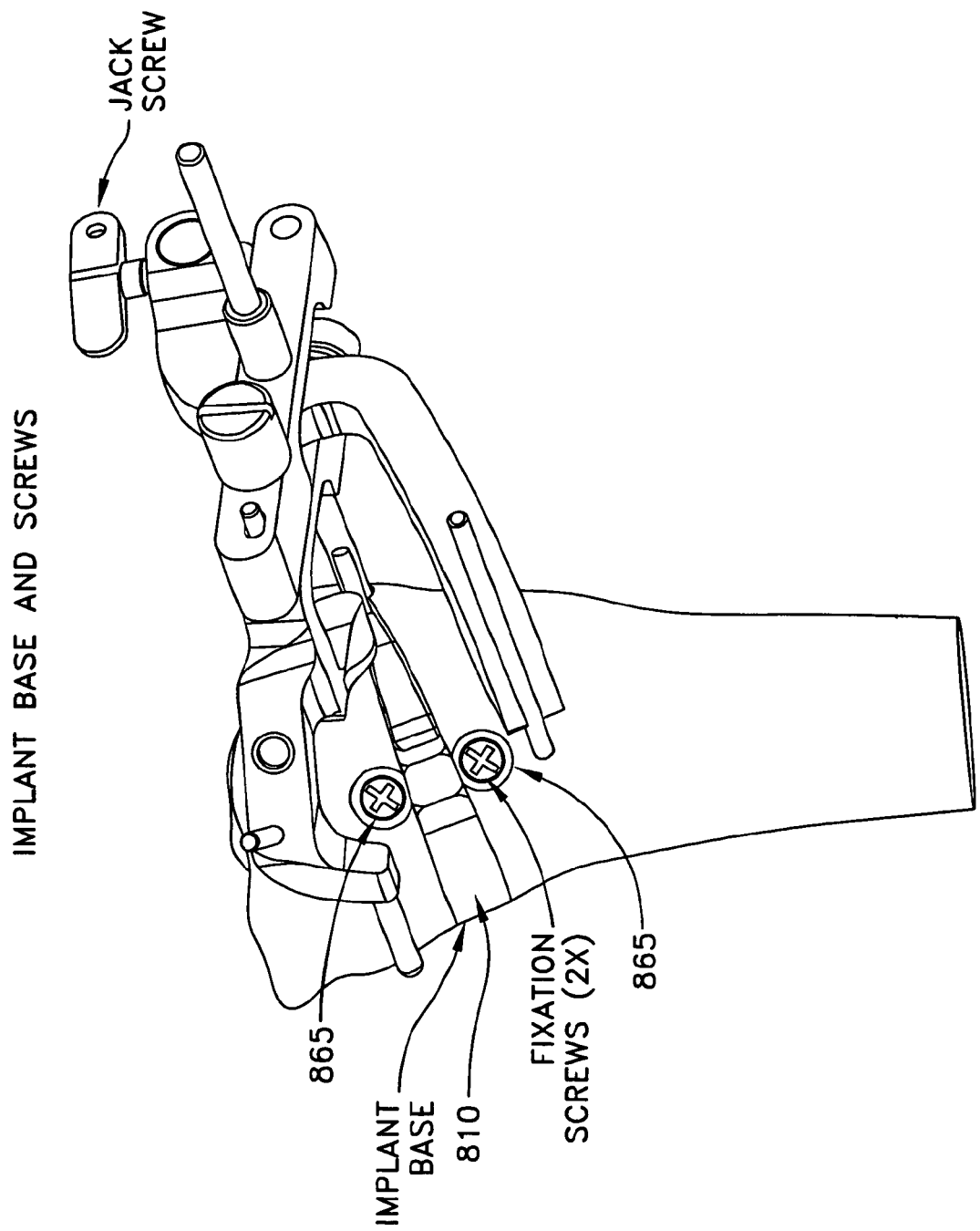

24. Then implant base 810 is inserted into the prepared osteotomy, with keys 820 and 825 seated in tibial holes 85 and 90, respectively. See FIG. 29. Keys 820 and 825, seating in tibial holes 85 and 90, help ensure a precise fit of the implant to the bone. As this is done, jack screw 735 is adjusted as necessary to facilitate insertion of the base into the osteotomy. Then jack screw 735 is tightened slightly to ensure that the implant components are fully seated into the osteotomy wedge. Next, fixation screws 865 are inserted through keys 820 and 825 in base 810 and into the tapped holes in the tibia, and tightened into place. See FIG. 30. Finally, opening jack 700, position guide 100, apex pin 300, distal pin 410, frontal pin 145 and A-M pin 150 are removed from the surgical site, and the incision closed.

Anterio-Lateral Osteotomies

In the foregoing description, the present invention is discussed in the context of performing an open wedge osteotomy using an antero-medial approach. Of course, it should be appreciated that the present invention may also be used in antero-lateral approaches, or other approaches which will be well known to those skilled in the art.

Figure 31:
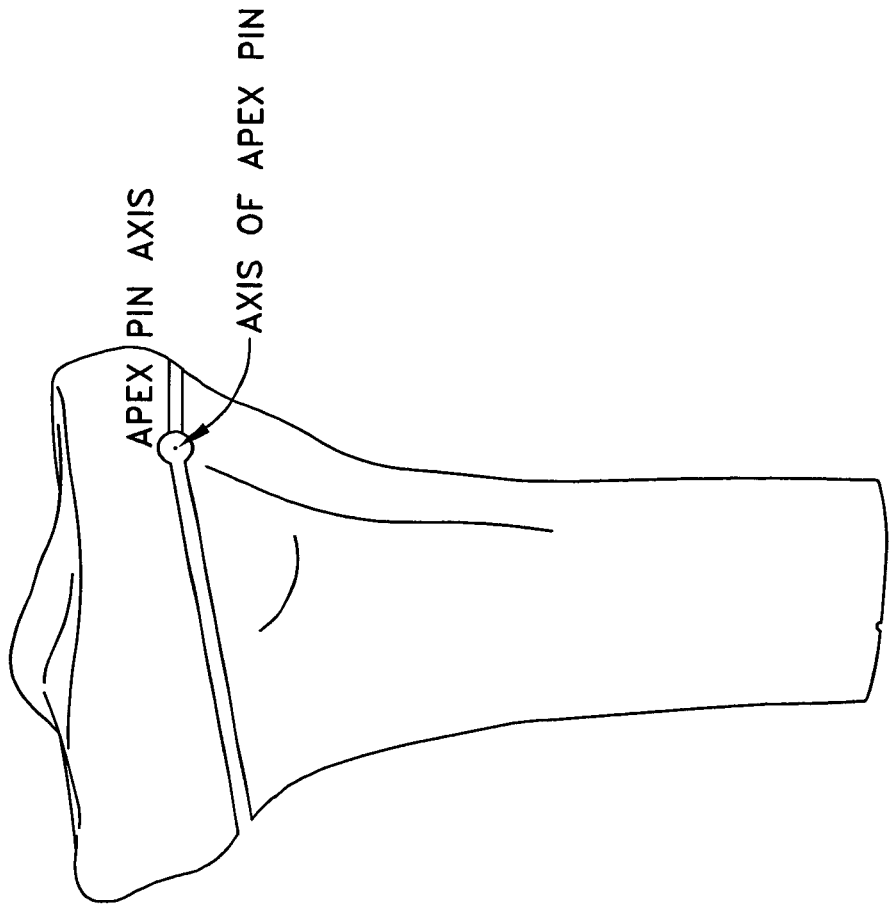
FIGS. 31-37 are schematic views showing various apex pin dispositions which may be used in connection with the open wedge, high tibial osteotomy.
Figure 32:
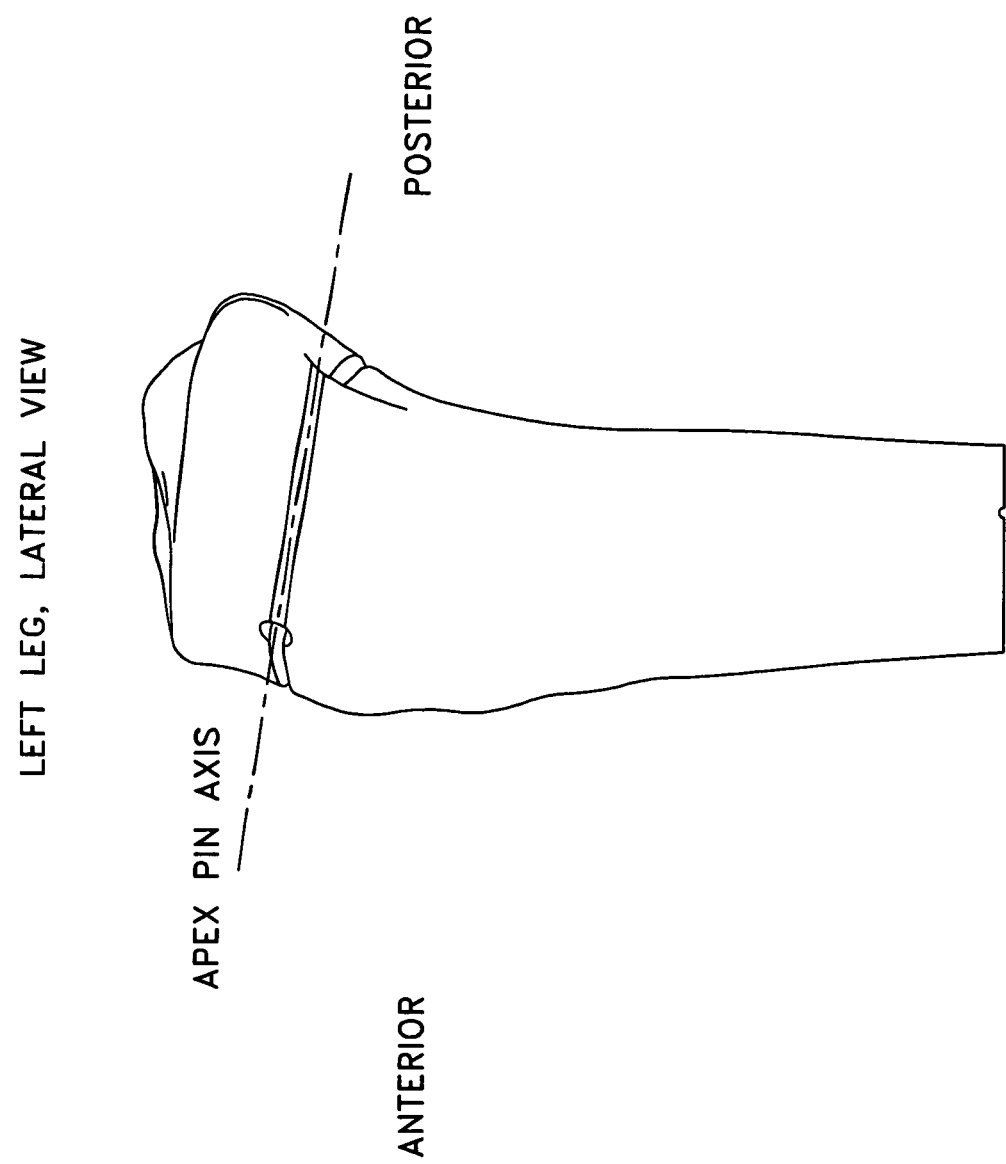

Method for Obtaining an Anterior-Posterior (A-P) Slope Correction in Conjunction with a Lateral-Medial (L-M) Correction in a High Tibial Osteotomy In the foregoing description, there was disclosed an approach for effecting a high tibial osteotomy in which the surgeon determines the anterior-posterior (A-P) slope of the tibia and determines the proper orientation of the osteotomy in relation to the frontal (i.e., coronal) plane of the tibia. After this is done, the surgeon places an apex pin into the tibia so as to precisely define the lateral limit of the osteotomy cut and hence the bony hinge of the osteotomy. The foregoing discussion identifies the importance of setting the apex pin parallel to the A-P tibial slope and perpendicular to the frontal (i.e., coronal) plane. See FIG. 31 which shows the apex pin perpendicular to the coronal plane, and FIG. 32 which shows the axis of the apex pin parallel to the A-P slope. Such an approach is important to prevent inadvertent or unintended changes to the A-P tibial slope as the alignment correction (and the opening of the osteotomy) is executed.

However, there may be situations in which the surgeon may deliberately wish to introduce an A-P slope change into the tibia, e.g., such as when resolving knee instability or knee ligament laxity.

The following disclosure describes an approach which allows the surgeon to make a quantifiable change to the A-P tibial slope. This approach essentially involves rotating the axis of the apex pin about the longitudinal axis of the tibia to a prescribed angle relative to the sagittal plane. This is in contrast to the preferred approach disclosed above, in which the axis of the apex pin is parallel to the sagittal plane.

Figure 33:
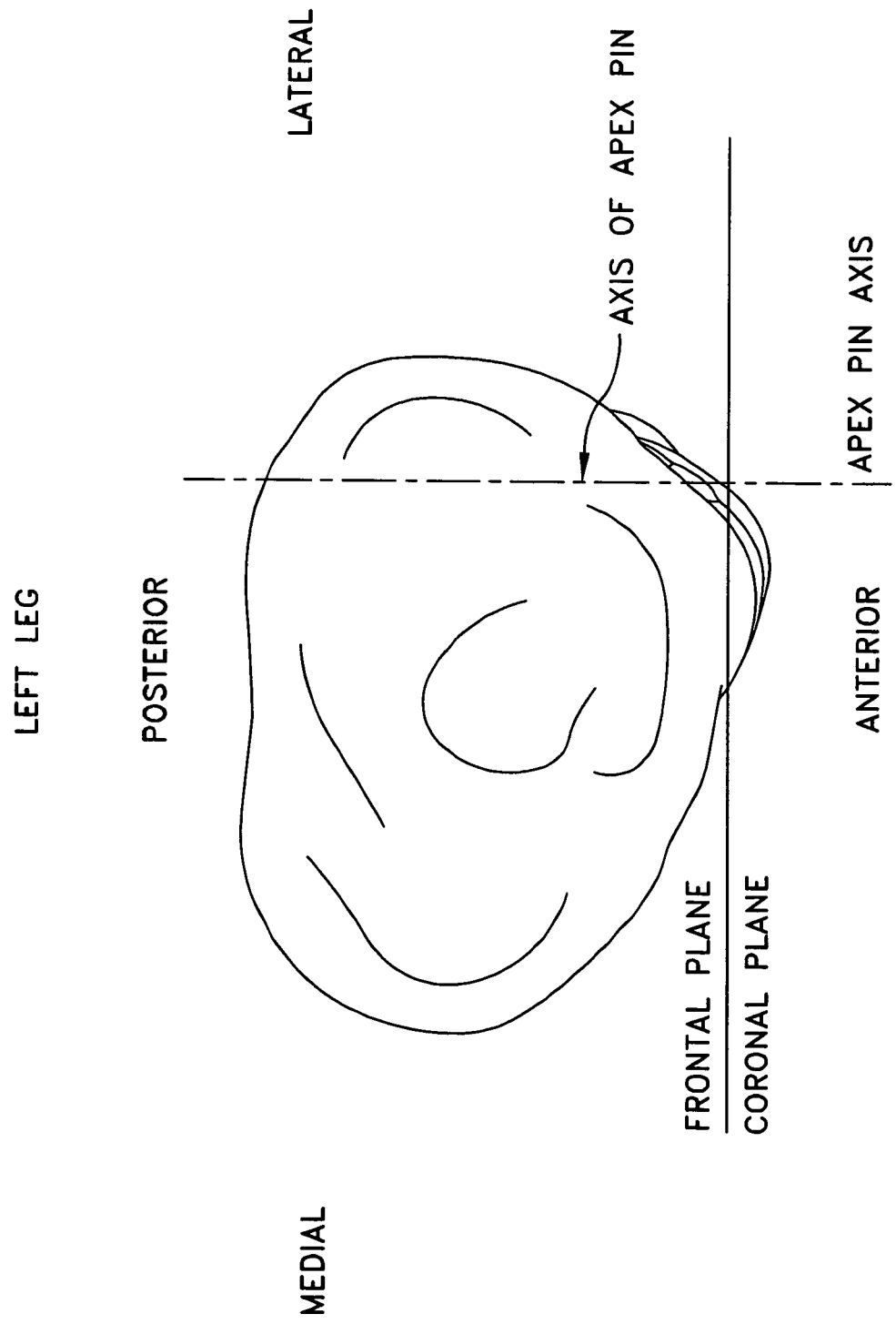

More particularly, FIG. 33 shows the axis of the apex pin disposed parallel to the sagittal plane. As noted previously, this orientation produces a lateral-medial (L-M) correction without affecting the A-P slope, since the inserted apex pin is parallel to the A-P slope.

Figure 34:
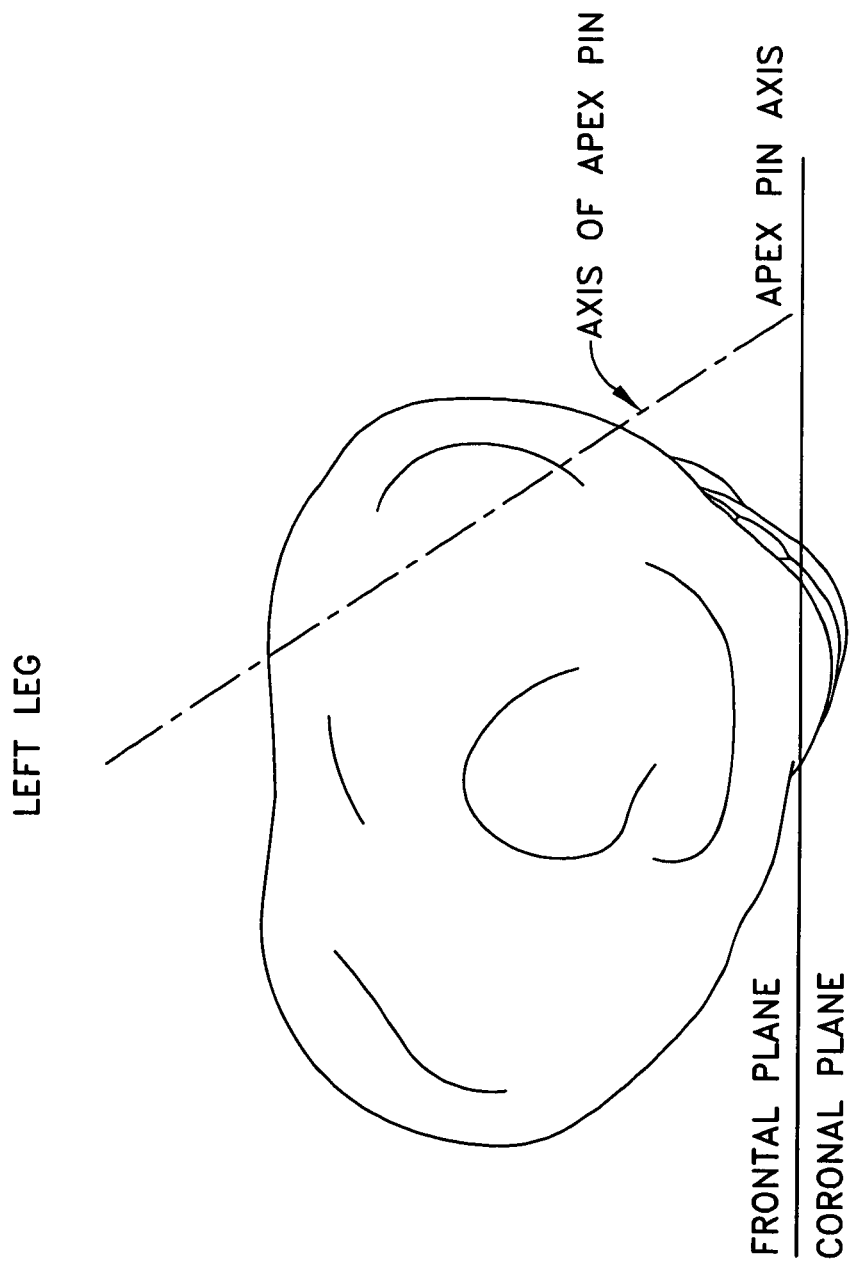

Looking now at FIG. 34, the axis of the apex pin is shown rotated in the posterior direction (i.e., counter-clockwise when seen from the top view of FIG. 34). This alternative orientation of the apex pin produces an increased A-P slope with a corresponding adjustment of the L-M slope. The resulting L-M and A-P slope corrections are a function of the total correction angle, i.e., the total amount that the axis of the apex pin is rotated relative to the sagittal plane.

Figure 35:
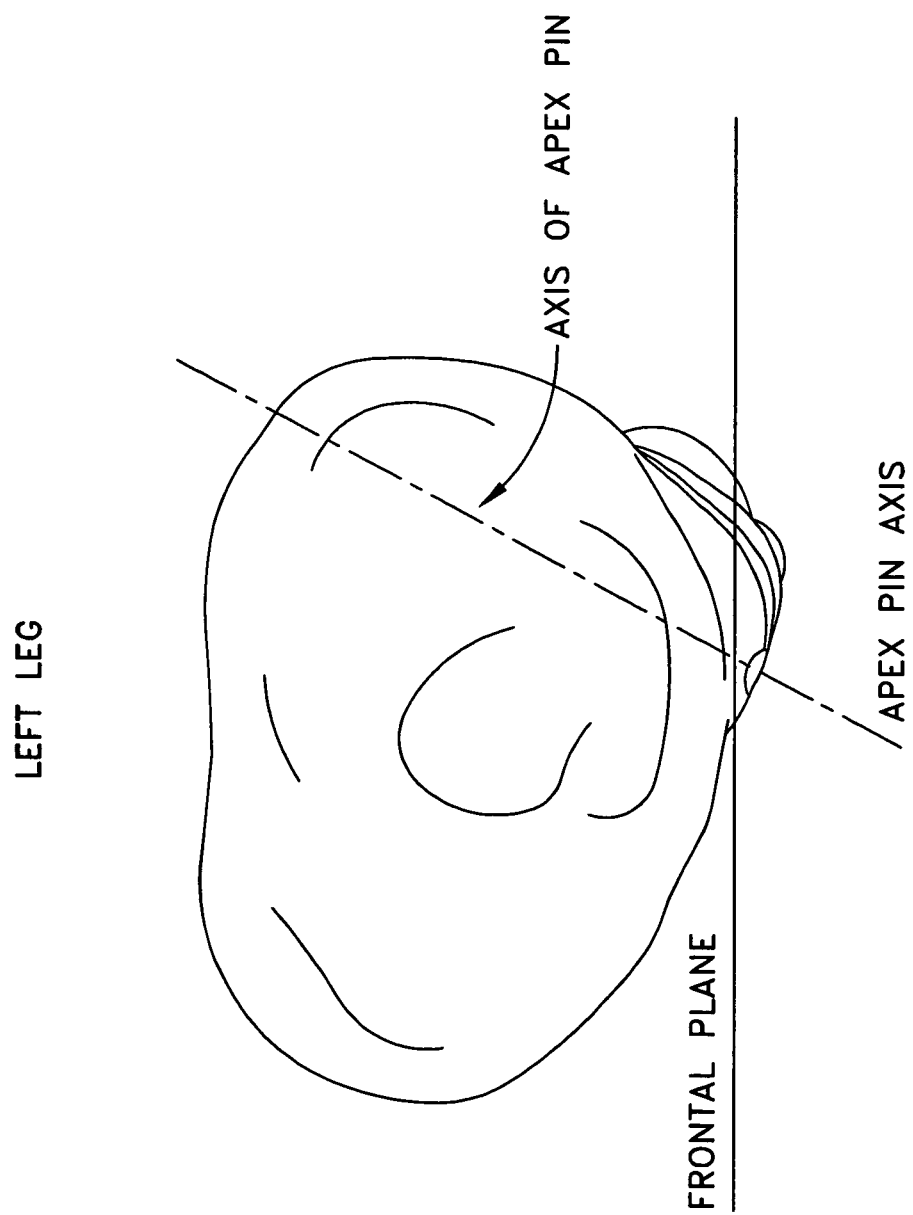

Looking now at FIG. 35, the axis of the apex pin is shown rotated in the anterior direction (i.e., clockwise when seen from the top view of FIG. 35). This alternative orientation of the apex pin produces a decreased A-P slope with a corresponding adjustment of the L-M slope. Again, the resulting L-M and A-P slope corrections are a function of the total correction angle, i.e., the total amount that the axis of the apex pin is rotated relative to the sagittal plane.

For discussion purposes, it can be assumed that there are no surgical limitations on the orientation of the apex pin. This allows the inspection of extreme orientations for the purposes of illustrating the operative concepts. From a surgical perspective, however, there are practical limitations to how far the apex pin can be rotated relative to the "standard" position (i.e., parallel to the sagittal plane). However, the following examples are valid for illustration purposes.

Figure 36:
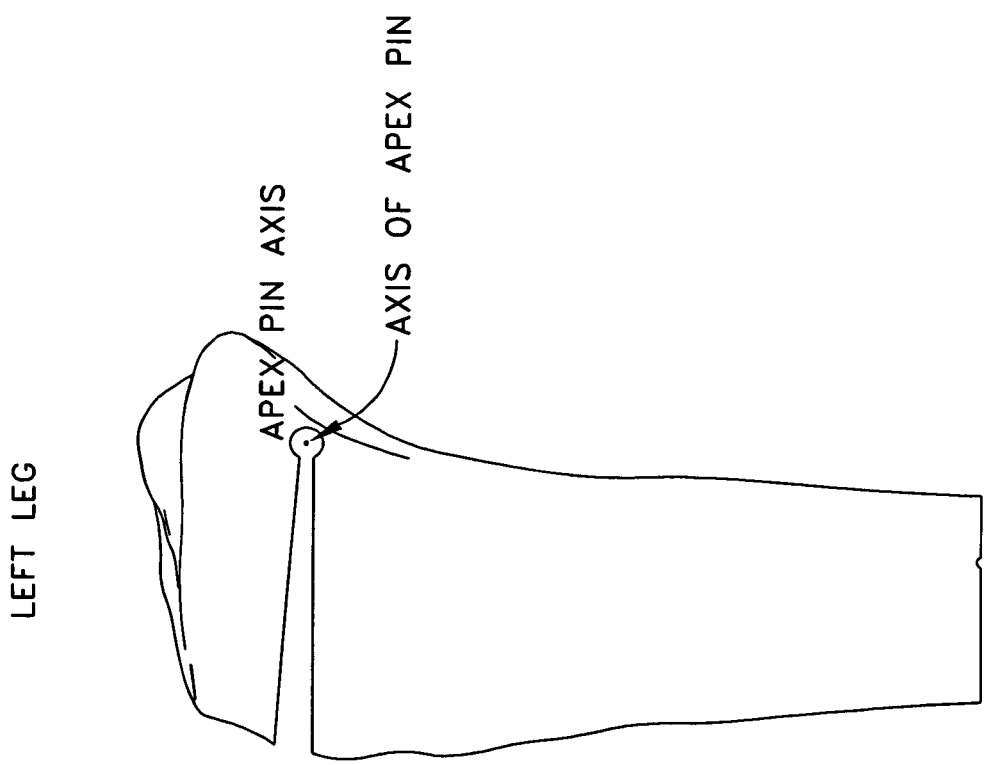

Looking now at FIG. 36, it becomes clear that if the apex pin is oriented posteriorly and parallel to the frontal (coronal) plane, the opening wedge osteotomy produces only A-P slope increases with no effect on the L-M slope.

Figure 37:
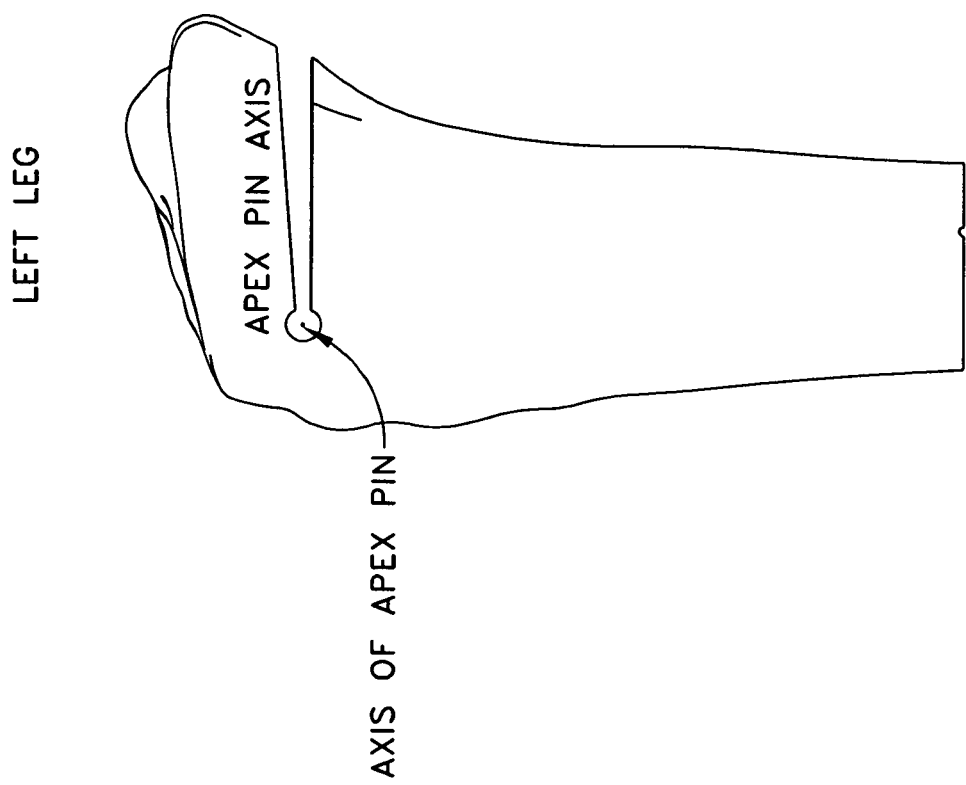

Similarly, and looking now at FIG. 37, an apex pin that is oriented anteriorly and parallel to the frontal (coronal) plane, produces only A-P slope decreases with no effect on the L-M slope.

It is clear from FIGS. 36 and 37 that, using this method, and interpolating between the extreme orientations, it is possible to obtain any combination of L-M slope, and either A-P slope increase and/or A-P slope decrease, by reorienting the apex pin relative to the sagittal plane.

An apex pin that is oriented 45° from the sagittal plane will necessarily produce equal L-M and A-P corrections for a given total correction angle. A 45° posterior orientation produces equal angle L-M increase and A-P increase. A 45° anterior orientation produces equal angle L-M increase and A-P decrease.

Furthermore, it can be shown that an apex pin located near the medial cortex instead of the lateral cortex will produce L-M slope changes in the opposite direction. This may be used for correcting a valgus malalignment.

Figure 38:
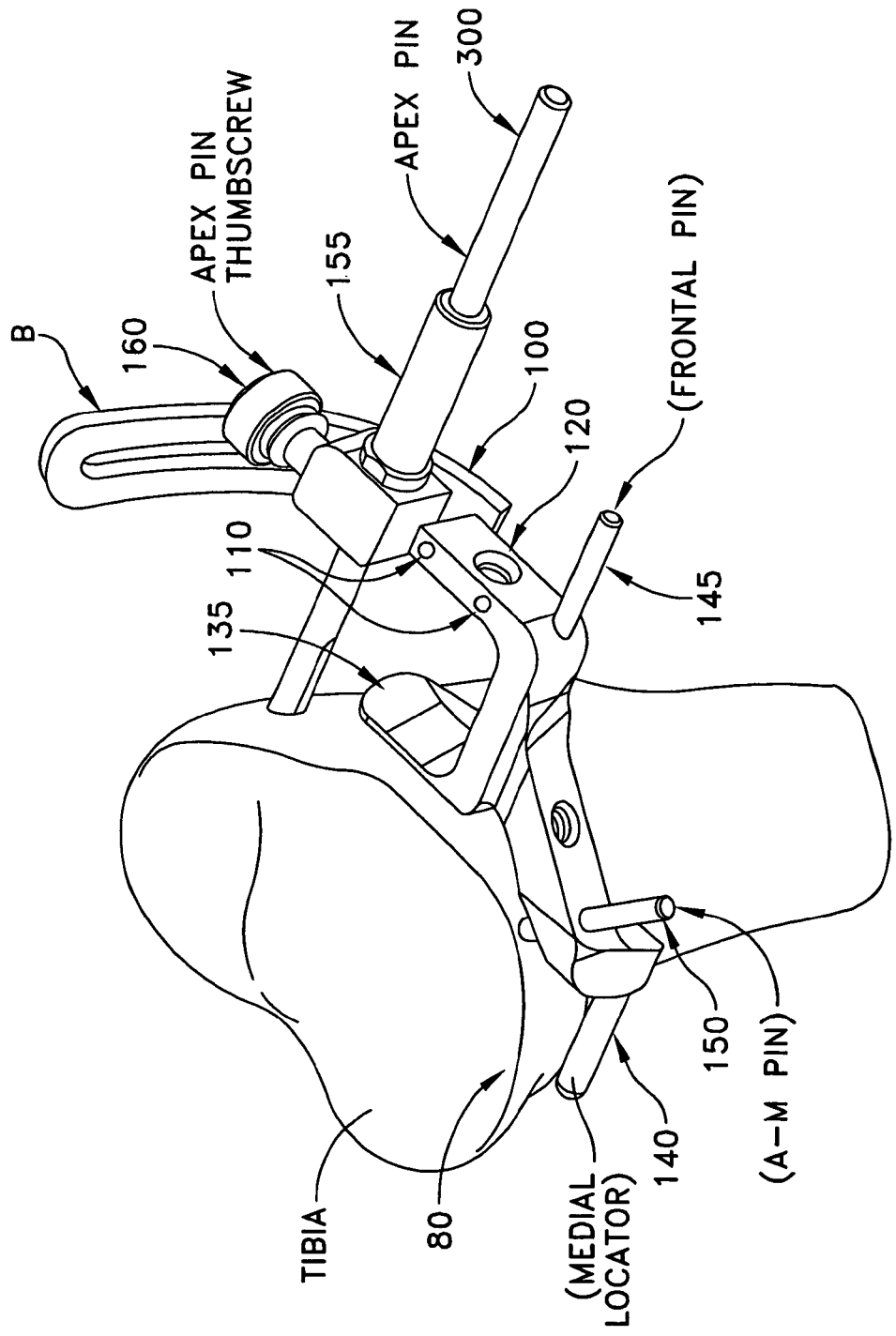
FIG. 38 is a schematic illustration showing how the disposition of the apex pin may be adjusted in accordance with the present invention.

Various constructions may be used to orient apex pin 300 with the desired angle relative to the sagittal plane. By way of example but not limitation, FIG. 38 shows how apex aimer 155 may be slidably mounted to a curved boom B so that the angle of apex pin may be adjusted relative to the sagittal plane. Other constructions will be apparent to those skilled in the art in view of the present disclosure.

Modifications

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A method for performing an open wedge, high tibial osteotomy, the method comprising:
    positioning a targeting apparatus for identifying a cutting plane through the tibia, defining an upper tibia portion and a lower tibia portion, and a boundary line for terminating a cut made along the cutting plane, wherein the boundary line is located within the tibia, parallel to the anterior-posterior slope of the tibia and at a selected angle to the sagittal plane of the patient;

cutting the bone along the cutting plane, with the cut terminating at the boundary line;

inserting a frontal pin into the upper bone portion;

inserting a distal pin into the lower bone portion;

arranging a jack to engage the frontal pin and the distal pin;

operating the jack to move the bone on either side of the cut apart by exerting force against the frontal pin and the distal pin so as to form the wedge-like opening in the bone; and stabilizing the bone.

2. A method according to claim 1 wherein the selected angle is established by translating the boundary line a selected degree in a counter-clockwise fashion so as to produce a change in the anterior-posterior slope and a change in the lateral-medial slope.

3. A method according to claim 1 wherein the selected angle is established by translating the boundary line a selected degree in a clockwise fashion so as to produce a change in the anterior-posterior slope and a change in the lateral-medial slope.

4. The method according to claim 1, further comprising providing an apex pin along the boundary line.

5. The method according to claim 1, further comprising, positioning a wedge-shaped implant in the wedge-shaped opening in the bone.

6. The method according to claim 5, wherein the jack remains in place while the wedge shaped implant is inserted into the wedge shaped opening.

7. The method according to claim 1, further comprising forming at least one keyhole adjacent to the cut.

8. The method according to claim 1, wherein the jack is operated by rotating a jack screw.

9. The method according to claim 1, wherein the targeting apparatus comprises the jack.

10. The method according to claim 1, further comprising manipulating the bone to assist in forming the wedge-like opening.

* * * * *